United States Patent
Marten et al.

(10) Patent No.: US 9,592,117 B2
(45) Date of Patent: Mar. 14, 2017

(54) COATED TRACHEOSTOMY TUBE AND STOMA STENT OR CANNULA

(75) Inventors: Lewis H. Marten, Westwood, MA (US); Dennis Creedon, Sandwich, MA (US)

(73) Assignee: E. BENSON HOOD LABORATORIES, Pembroke, MA (US)

( * ) Notice: Subject to any disclaimer, the term of this patent is extended or adjusted under 35 U.S.C. 154(b) by 1984 days.

(21) Appl. No.: 12/234,031

(22) Filed: Sep. 19, 2008

(65) Prior Publication Data

US 2009/0062927 A1    Mar. 5, 2009

Related U.S. Application Data

(63) Continuation-in-part of application No. 11/440,905, filed on May 25, 2006, now abandoned.

(51) Int. Cl.

| | |
|---|---|
| *A61M 11/00* | (2006.01) |
| *A61F 2/20* | (2006.01) |
| *A61F 2/94* | (2013.01) |
| *A61F 5/08* | (2006.01) |
| *A61M 16/04* | (2006.01) |

(52) U.S. Cl.
CPC ............... *A61F 2/203* (2013.01); *A61F 2/94* (2013.01); *A61F 5/08* (2013.01); *A61M 16/0465* (2013.01); *A61F 2230/0067* (2013.01); *A61F 2230/0078* (2013.01); *A61M 16/0468* (2013.01); *A61M 16/0488* (2013.01); *A61M 2205/0222* (2013.01)

(58) Field of Classification Search
CPC .... A61F 2/203; A61F 2/94; A61F 5/08; A61F 2230/0078; A61F 2230/0067; A61M 16/0465; A61M 16/0488; A61M 2205/0222; A61M 16/0468
USPC .... 128/207.14, 858, 207.18, 200.24, 200.26, 128/203.22, 206.11, 207.13; 606/191, 606/196, 199, 108; 604/541, 540
See application file for complete search history.

(56) References Cited

U.S. PATENT DOCUMENTS

| | | | | |
|---|---|---|---|---|
| 3,935,859 | A | * | 2/1976 | Doyle ............................ 606/196 |
| 5,350,396 | A | * | 9/1994 | Eliachar ........................ 606/199 |
| D354,814 | S | * | 1/1995 | Doyle ........................... D24/190 |
| 5,983,898 | A | * | 11/1999 | Doyle ............................ 128/858 |
| D468,826 | S | * | 1/2003 | Doyle ............................ D24/128 |
| 6,569,110 | B2 | * | 5/2003 | Bernard et al. ................... 602/5 |
| 7,441,559 | B2 | * | 10/2008 | Nelson et al. ................. 128/848 |
| 8,092,478 | B2 | * | 1/2012 | Kotler ............................ 606/191 |

\* cited by examiner

*Primary Examiner* — Steven Douglas
(74) *Attorney, Agent, or Firm* — Frommer Lawrence & Haug LLP

(57) ABSTRACT

The present invention relates to devices used in the management of bodily airways including tracheostomy tubes, laryngectomy tubes, bronchial stents, bronchial Y-tubes, bronchial TY-tubes, and nasal stents. The devices may comprise a protective coating to prevent the accumulation of mucus, crusting and granulation on or around airway management devices, as well as prevent adhesion to tissues which can cause bleeding upon removal, and prevent build-up of blood, or blood clots, to the stent.

14 Claims, 38 Drawing Sheets

Protective Coating

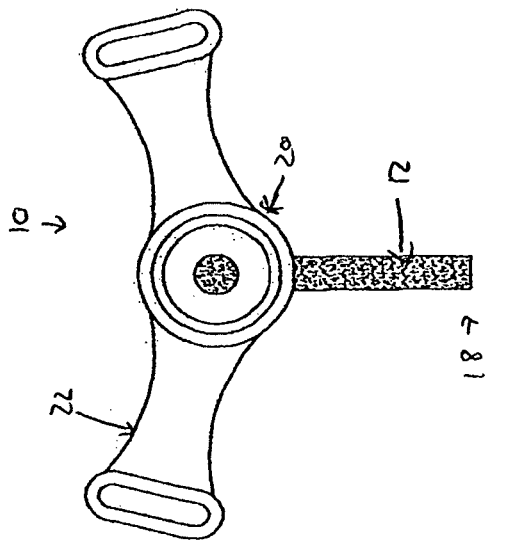
Fig. 3 FRONT VIEW
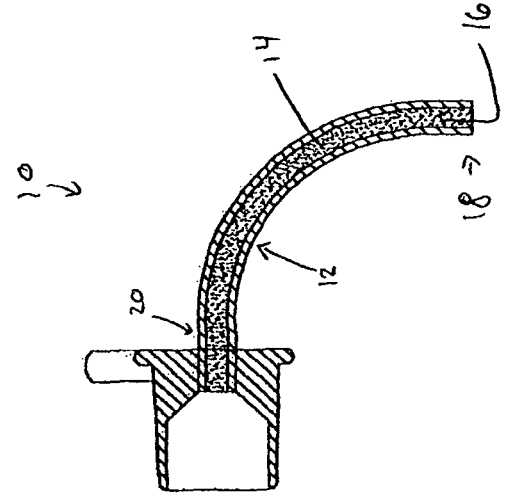
Fig. 2 CUT AWAY VIEW OF THE TRACHEOSTOMY TUBE
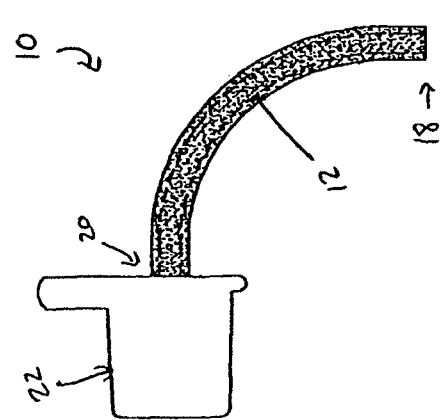
Fig. 1 SIDE VIEW
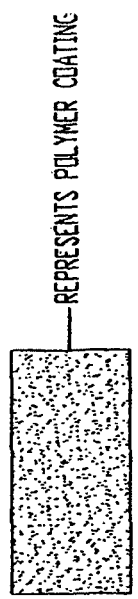
REPRESENTS POLYMER COATING

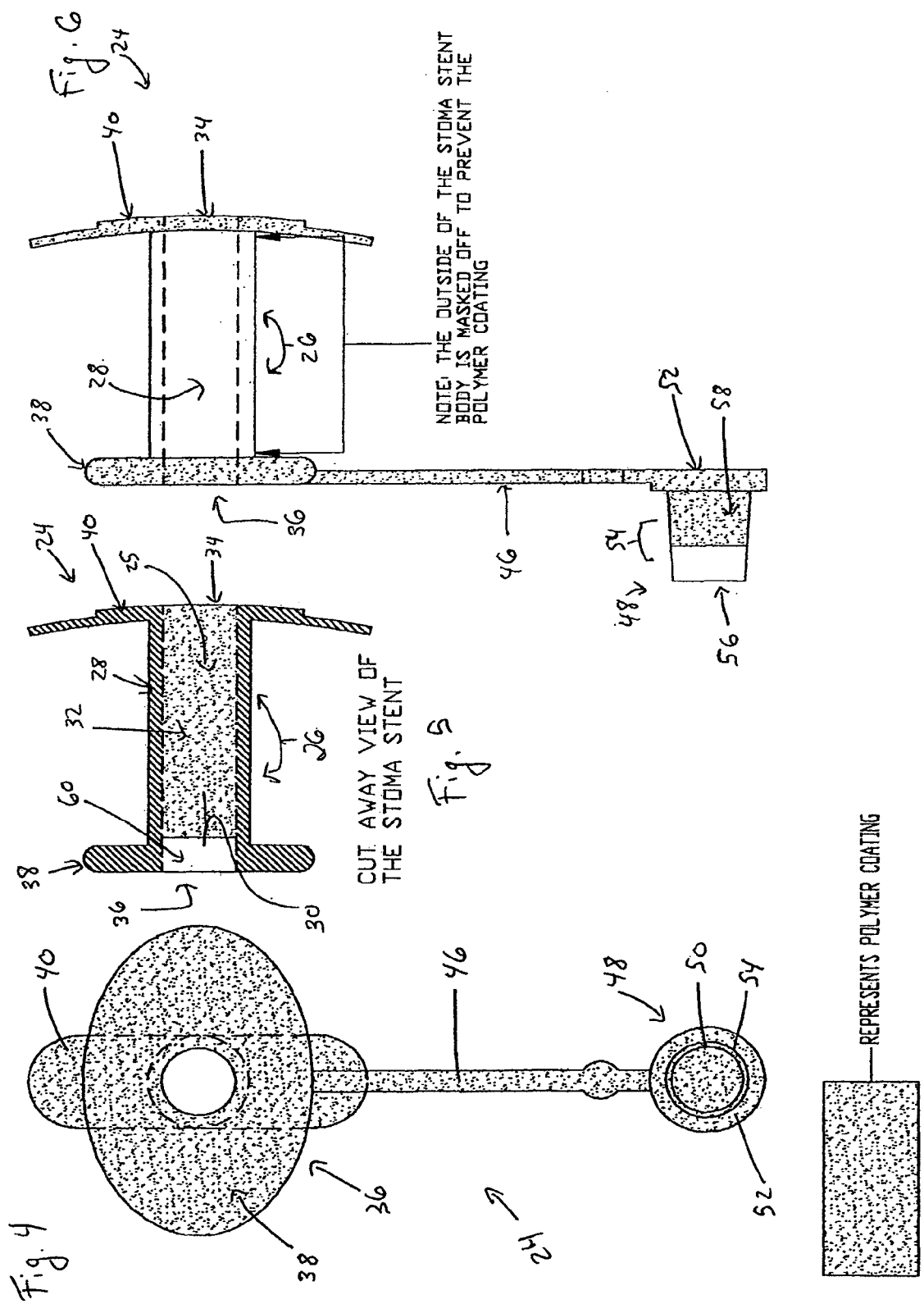

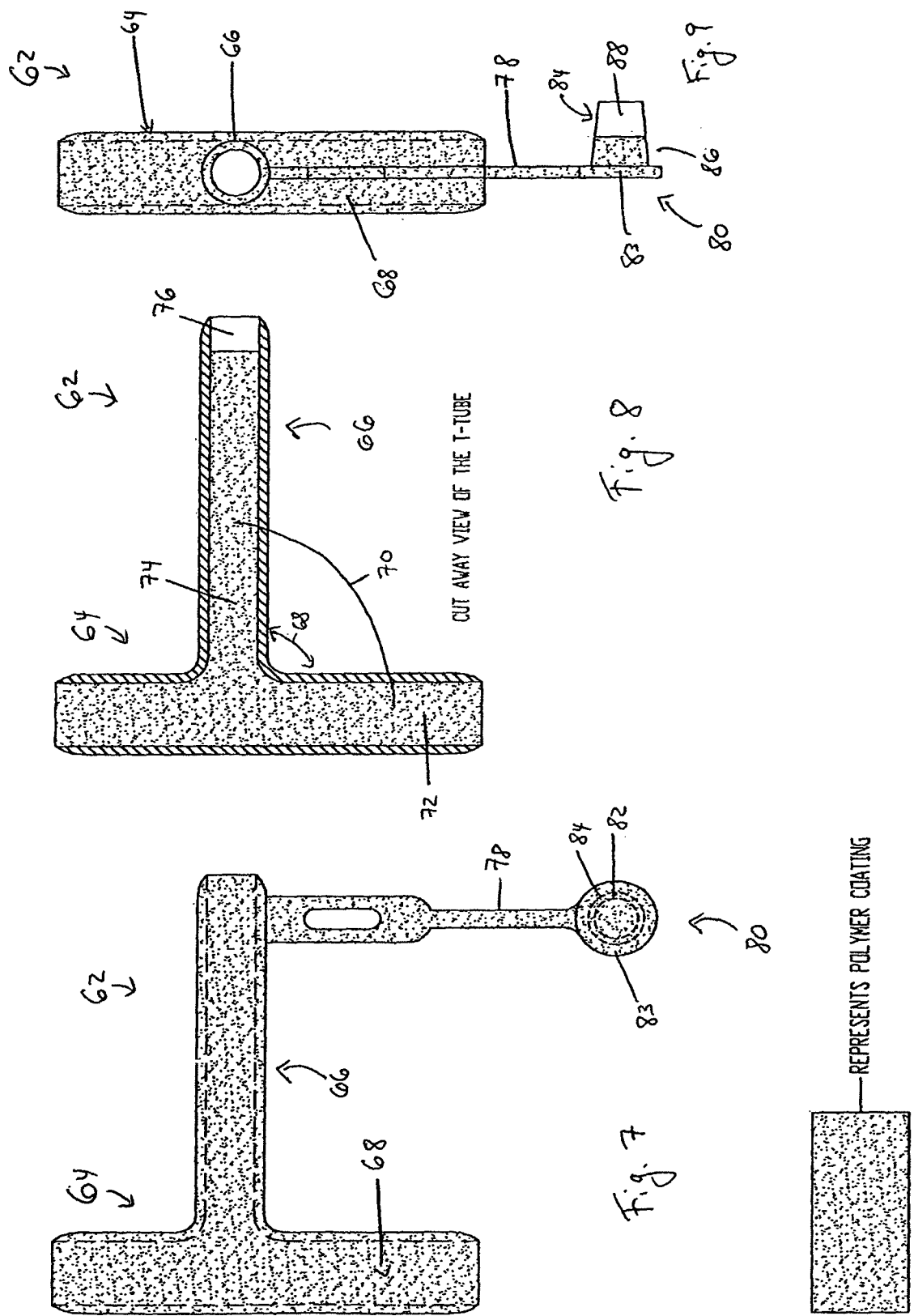

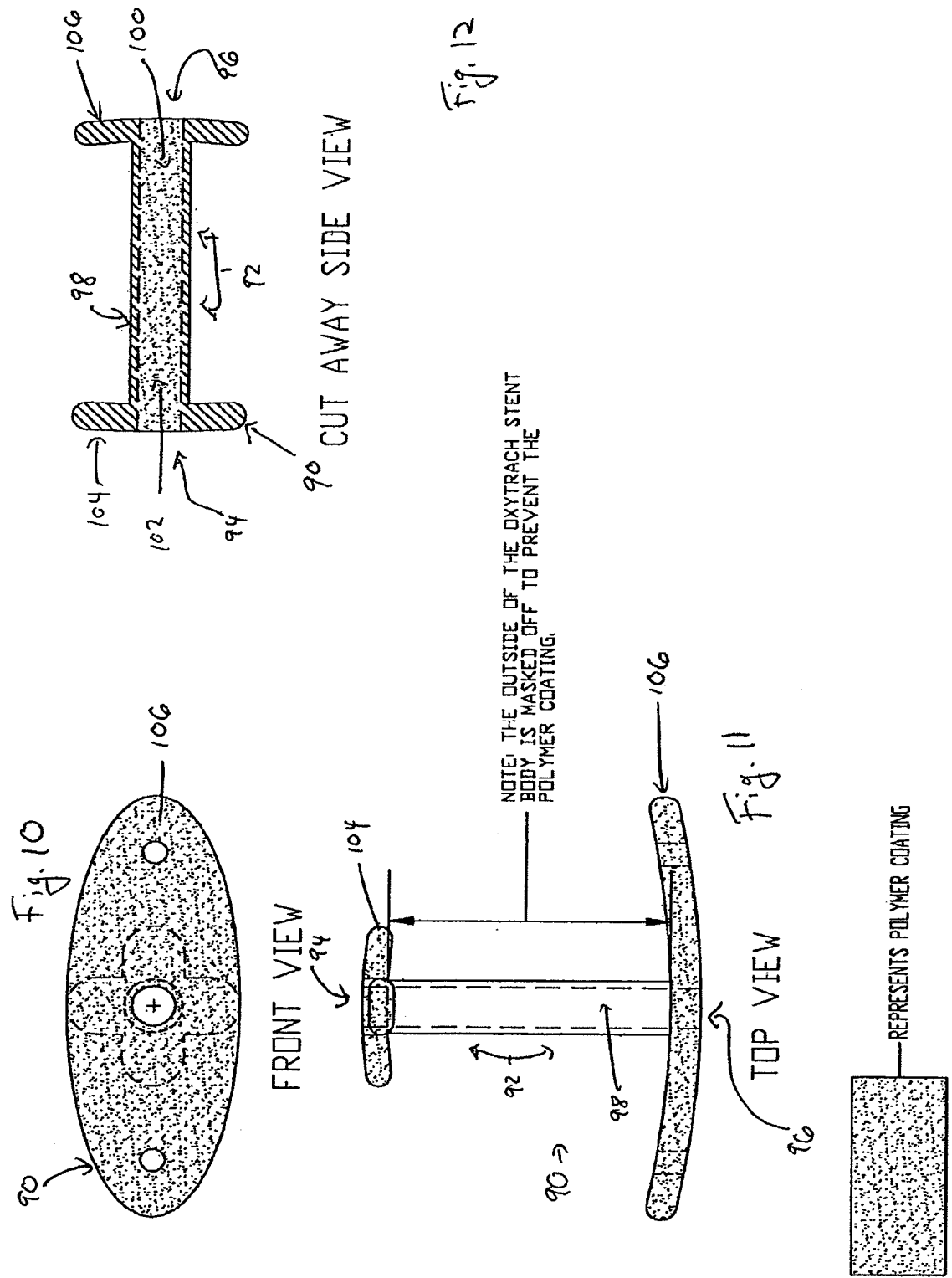

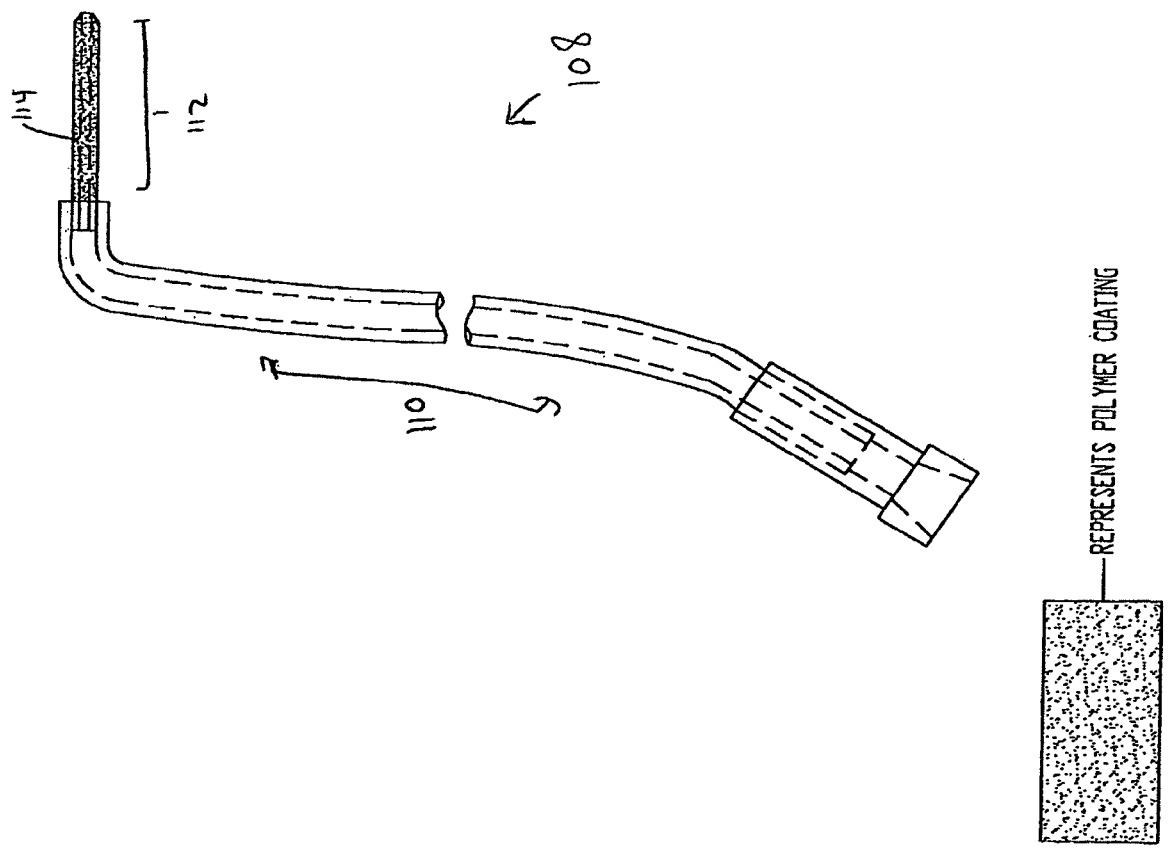

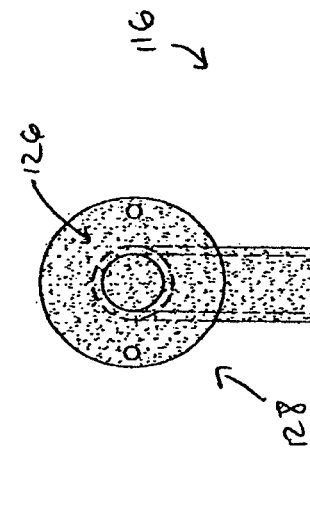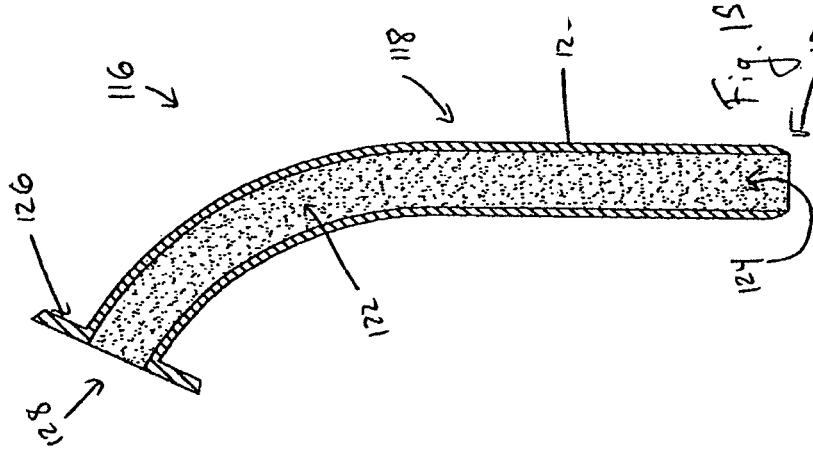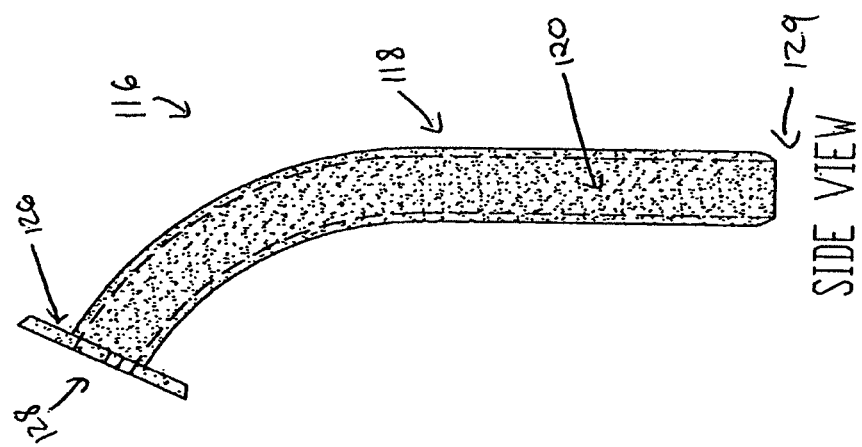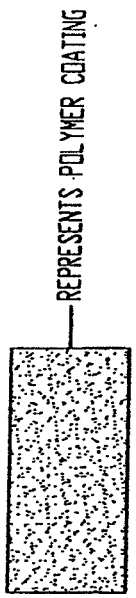

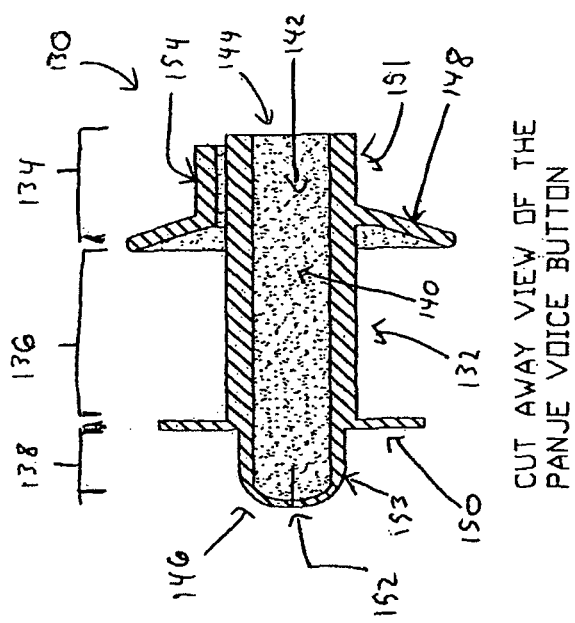
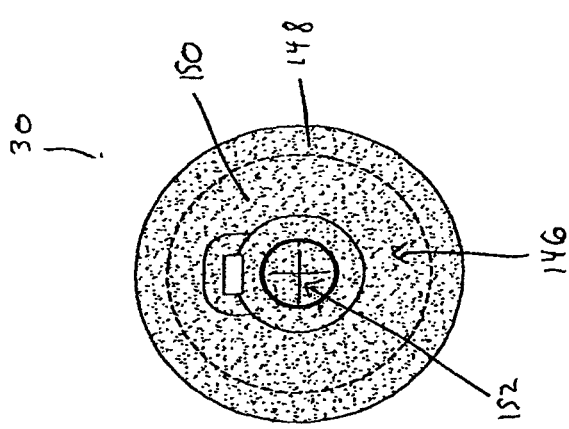
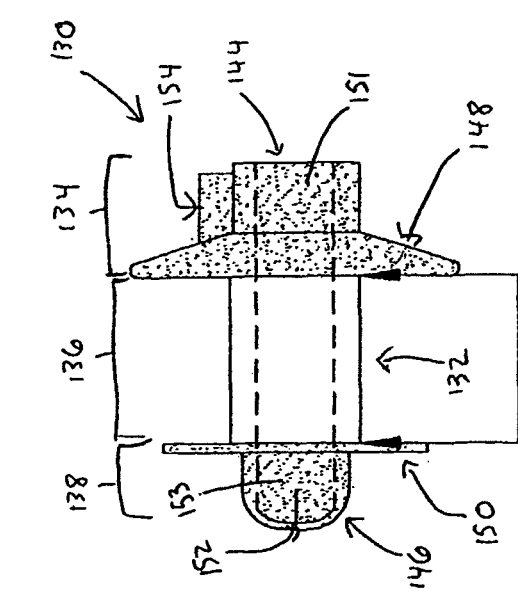
Fig. 17 — Cut away view of the Panje Voice Button
Fig. 18
Fig. 17 — Note: The outside of the Panje voice button body is masked off to prevent the polymer coating
Represents polymer coating

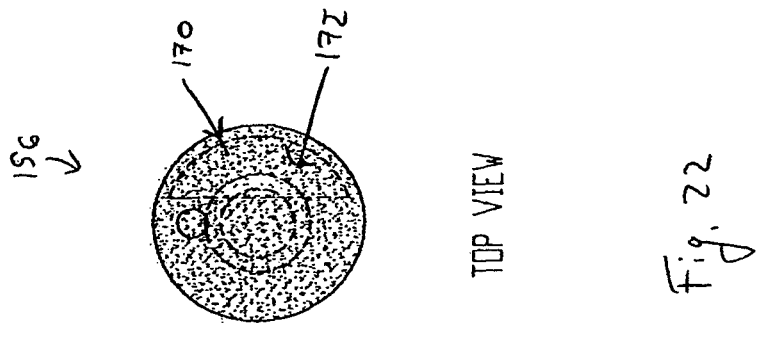
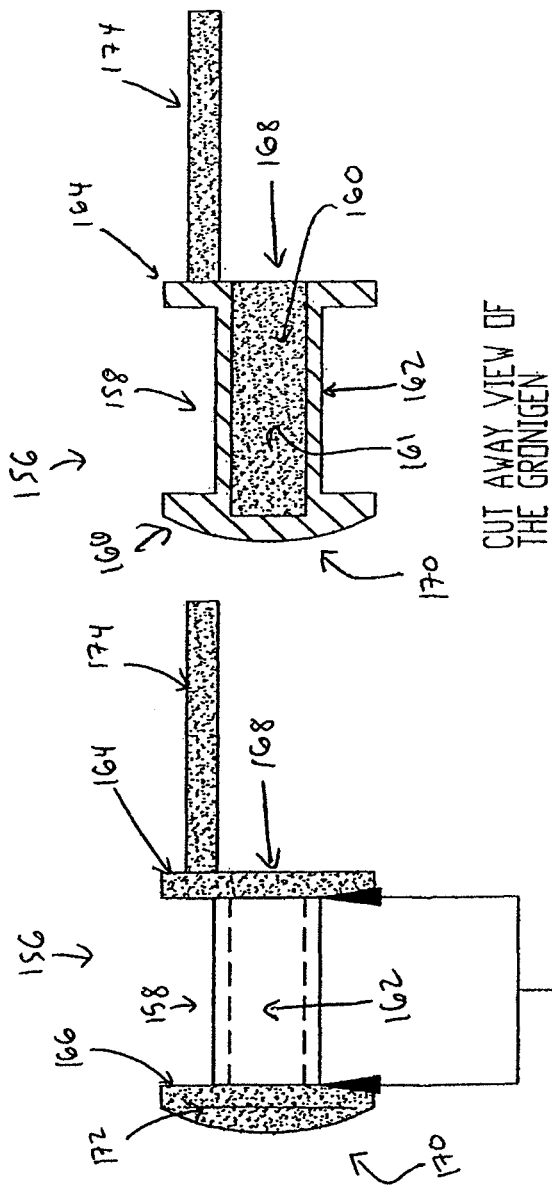
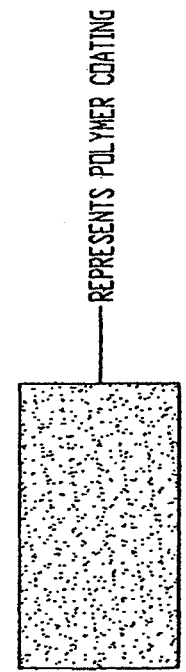

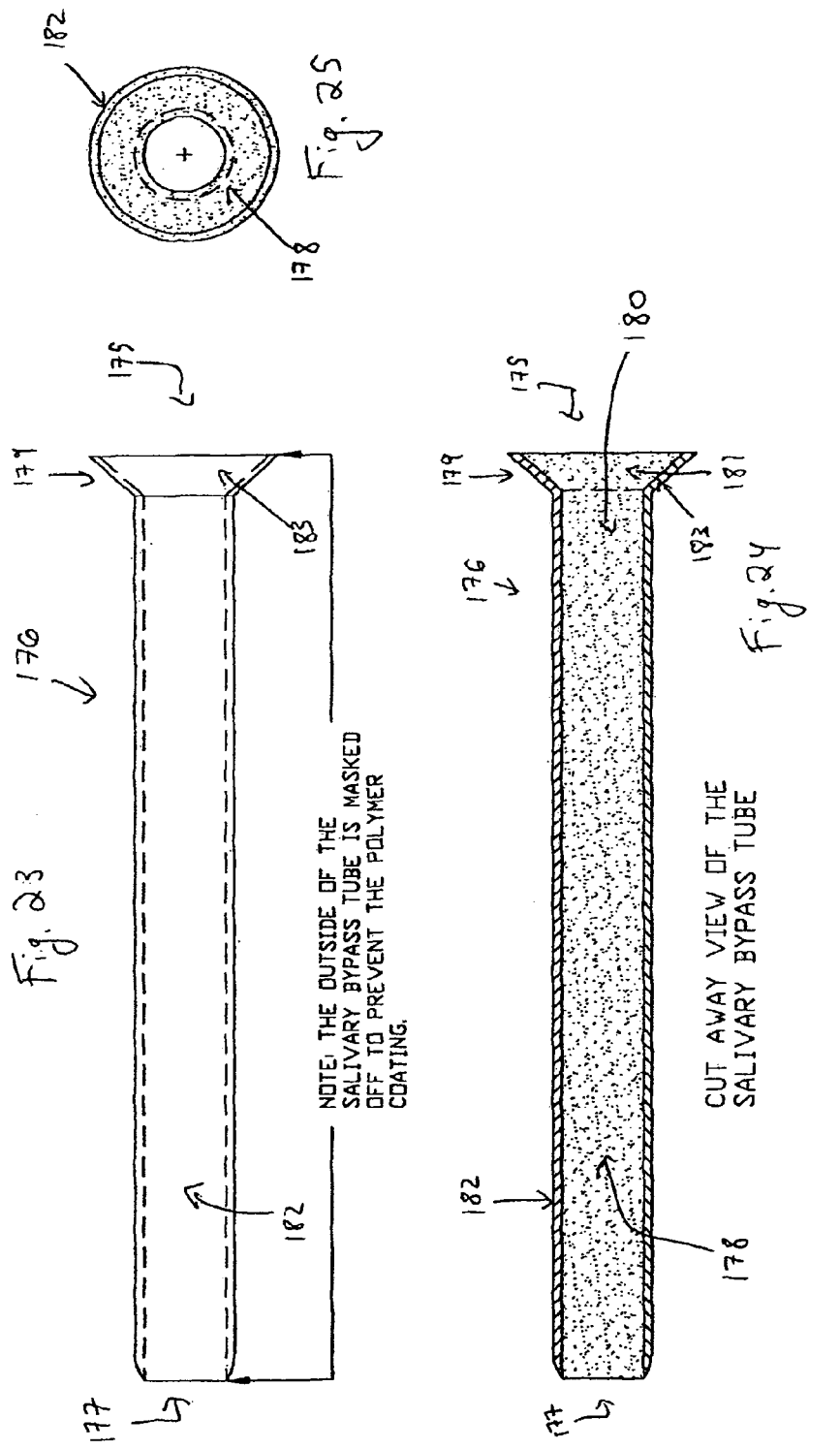

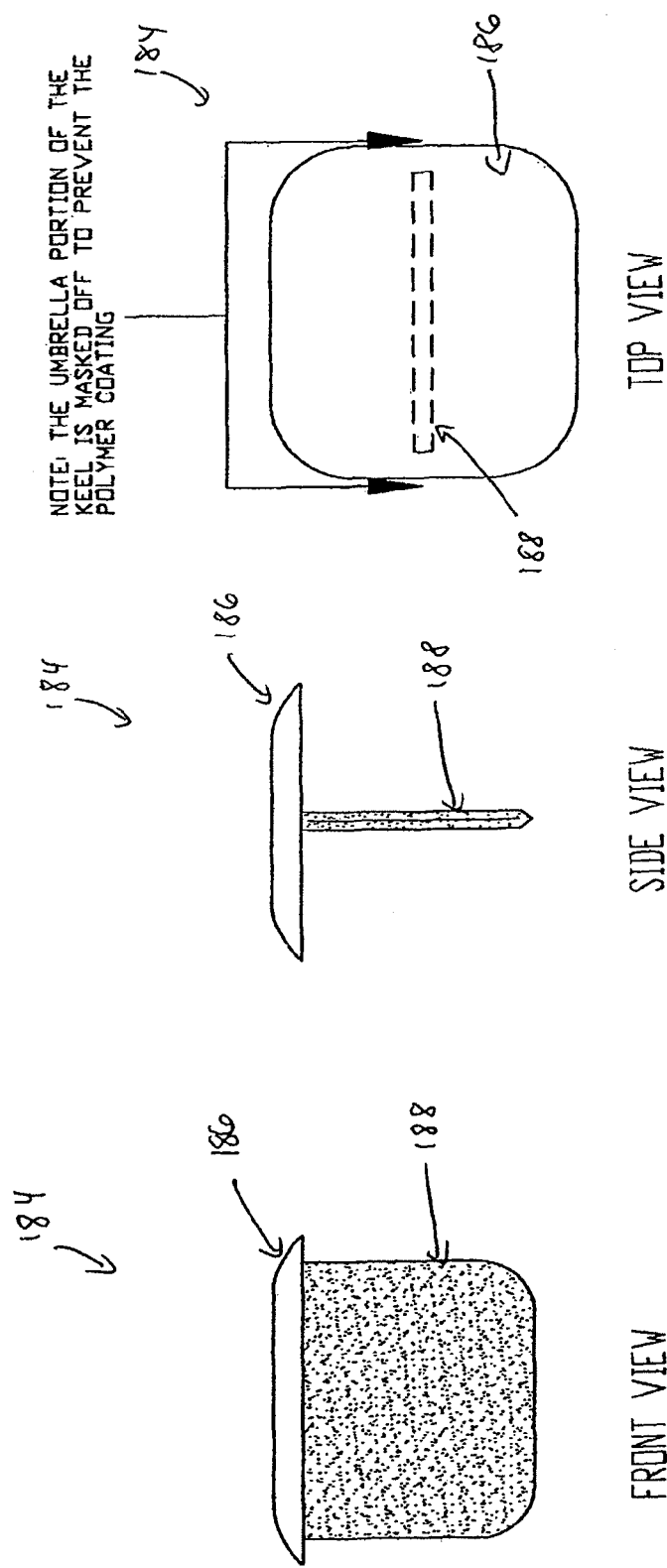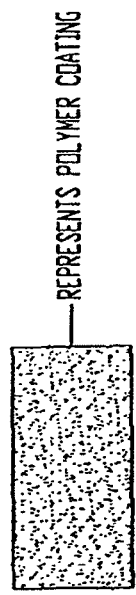

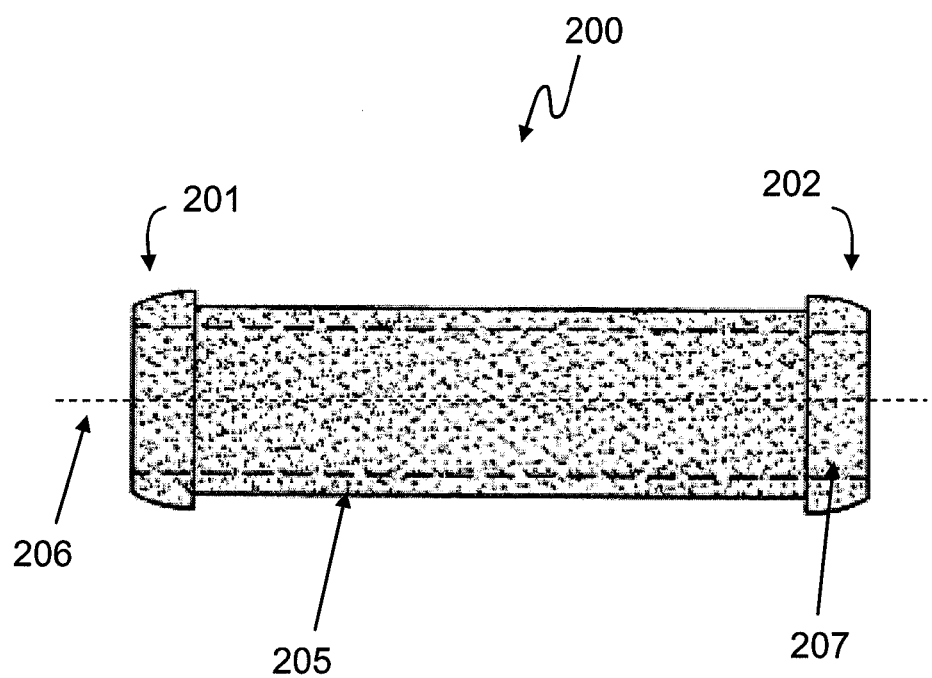
 Protective Coating
FIG. 31

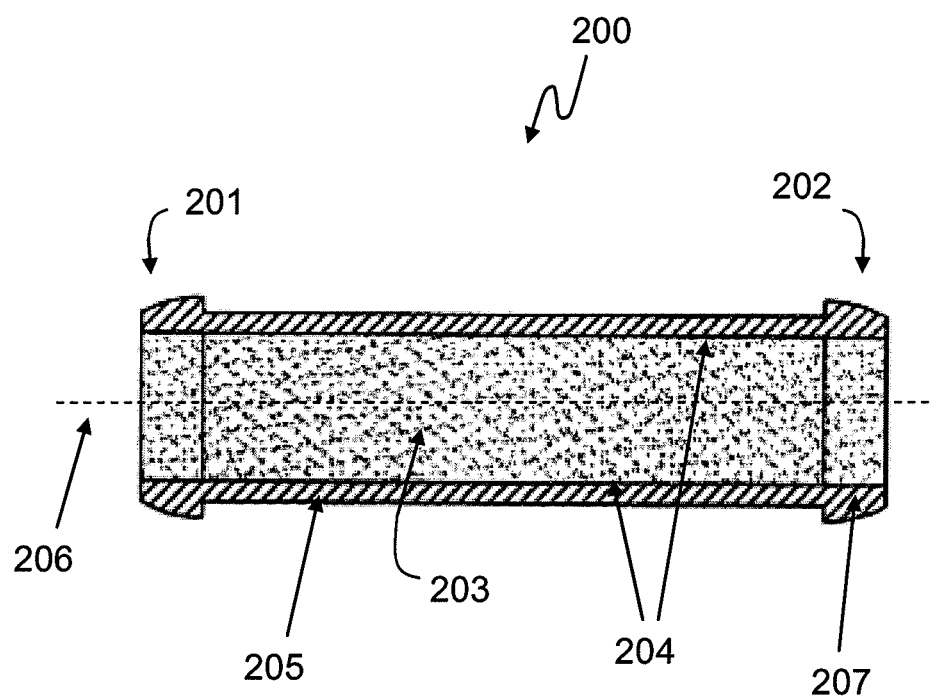
 Protective Coating
FIG. 32

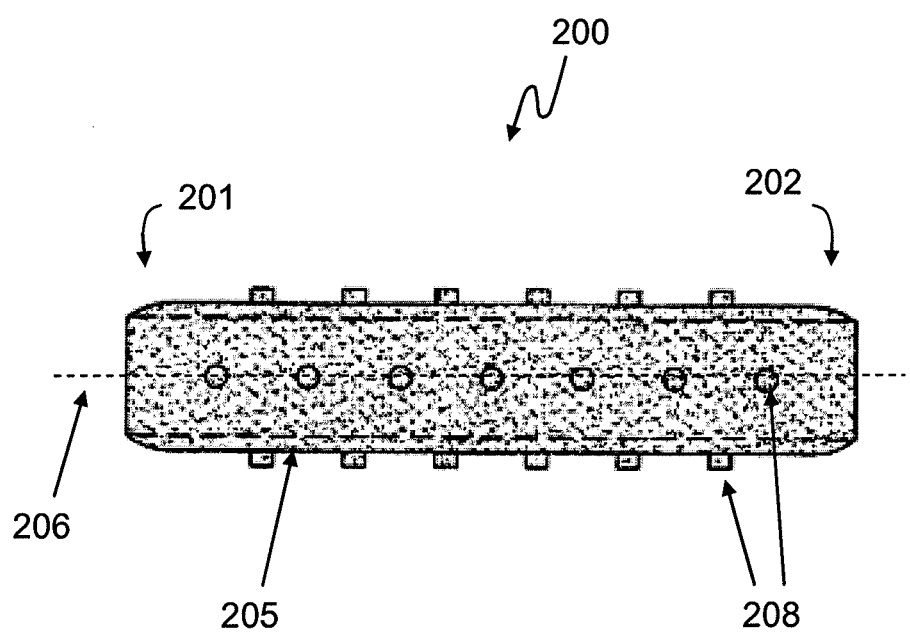
 Protective Coating
FIG. 33

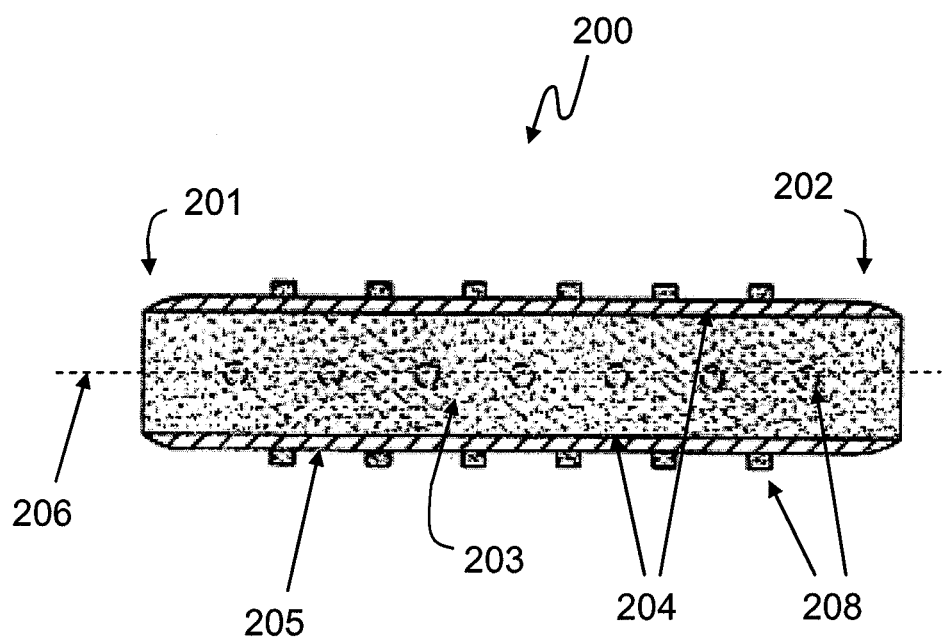
 Protective Coating
FIG. 35

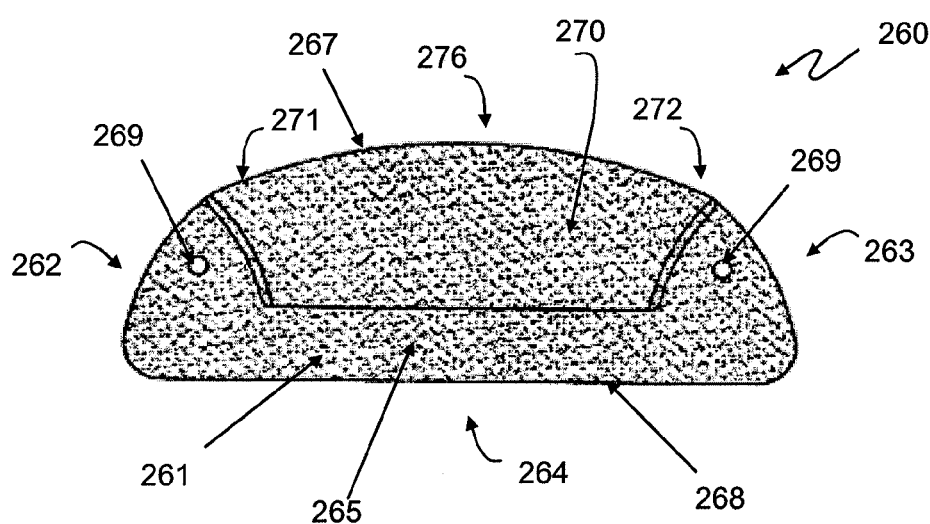
 Protective Coating
FIG. 43

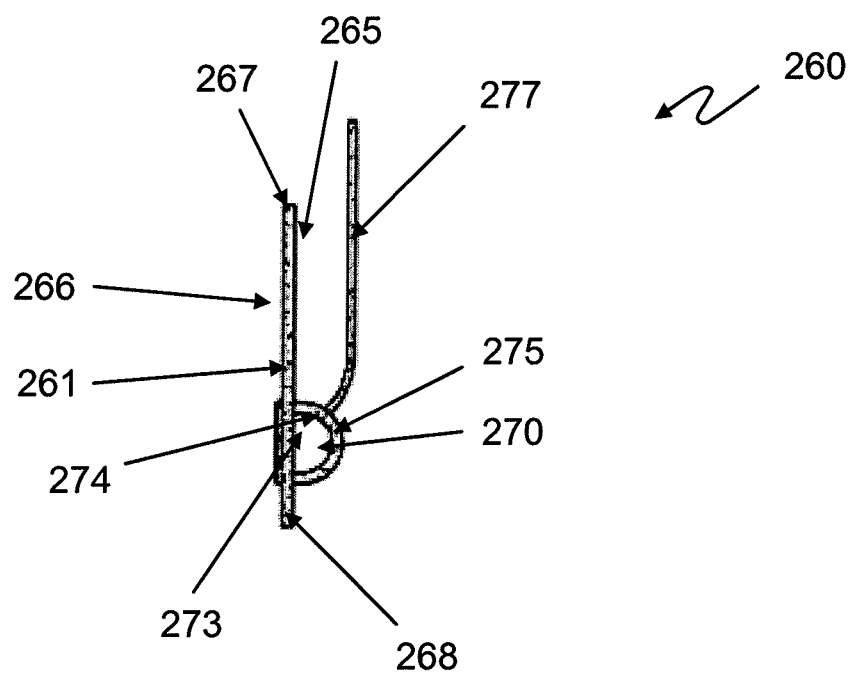
 Protective Coating
FIG. 46

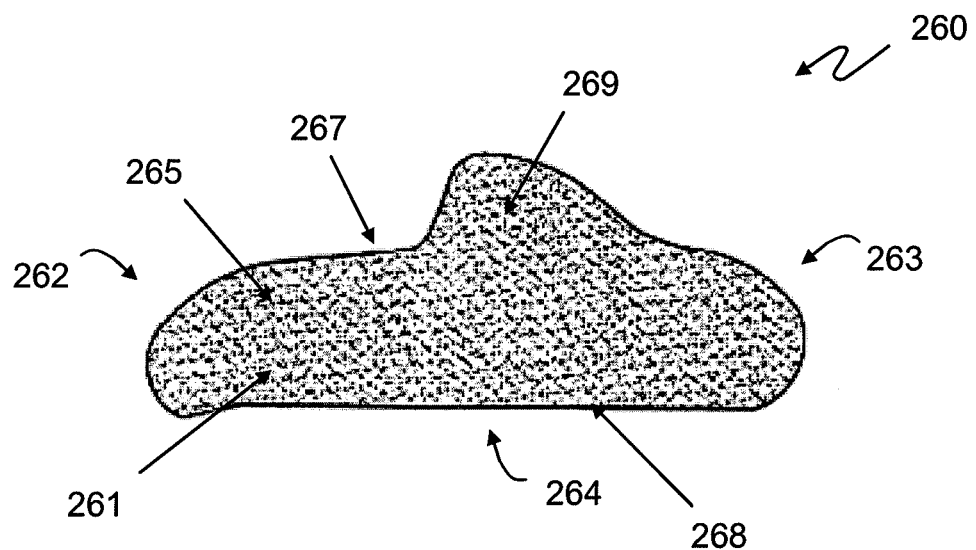
 Protective Coating
FIG. 48

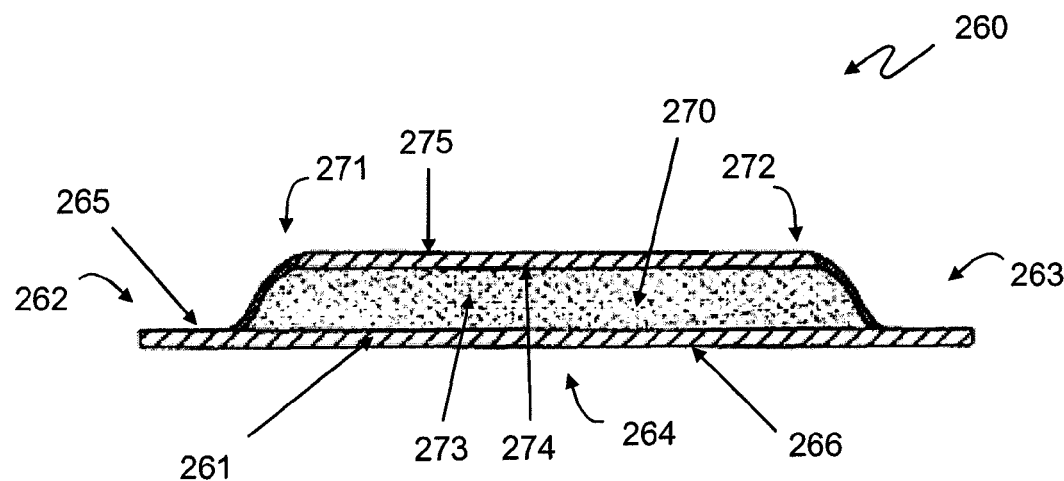
 Protective Coating
FIG. 53

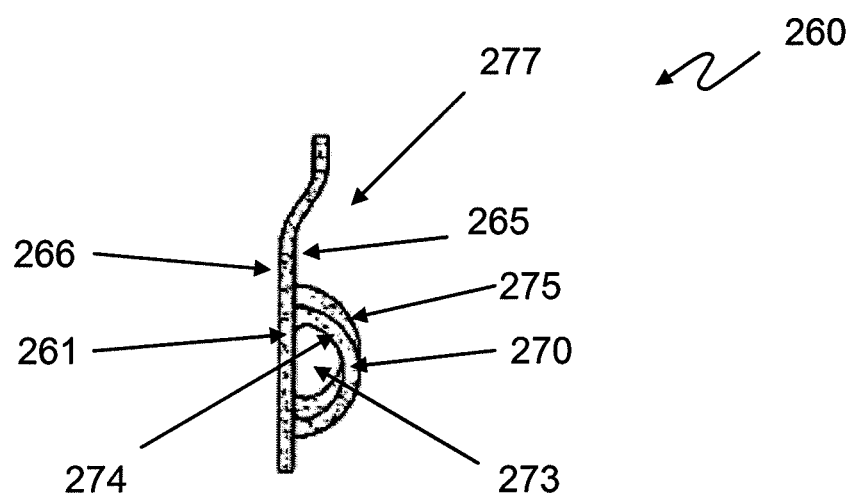
 Protective Coating
FIG. 55

COATED TRACHEOSTOMY TUBE AND STOMA STENT OR CANNULA

INCORPORATION BY REFERENCE

This application is a continuation-in-part of, and claims priority to, U.S. patent application Ser. No. 11/440,905 filed May 25, 2006, now abandoned.

The foregoing application, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to devices used in the management of bodily airways including tracheostomy tubes, laryngectomy tubes, bronchial stents, bronchial Y-tubes, bronchial TY-tubes, and nasal stents. The devices may comprise a protective coating to prevent the accumulation of mucus, crusting and granulation on or around airway management devices, as well as prevent adhesion to tissues which can cause bleeding upon removal, and prevent build-up of blood, or blood clots, to the stent.

BACKGROUND OF THE INVENTION

A wide variety of airway management devices exist. Airway management devices may be used for a variety of reasons including the facilitation of speaking and breathing following a laryngectomy, the promotion of healing in the patient, the provision of an access point for forced ventilation of a patient, and a variety of other uses including supplying oxygen to augment normal breathing. In particular, attention is directed to tracheostomy tubes and devices used in conjunction with airways, for example, stoma stents, tracheal T-tubes, transtracheal oxygen stents, bronchial stents, and nasal splints, among others.

Tracheostomy tubes are used to administer positive-pressure ventilation, to protect against aspiration, to provide an airway in patients prone to upper airway obstruction, and to provide access to the lower respiratory tract for airway clearance. Tracheostomy devices may be designed to be used with an inner cannula. The inner cannula is inserted into the tube or outer cannula, and is used to maintain the airway provided by the outer cannula as clean. The inner cannula may be disposable or may be reusable such that it is cleaned or replaced periodically with a new inner cannula. The inner cannula can be a low-profile inner cannula which is used for spontaneous breathing, or an inner cannula with a connector to attach a ventilator.

Stoma stents are prostheses that are held in place in the stoma following a tracheostomy to help maintain patency of the tracheostomy. Bronchial stents are prostheses that relieve an area of obstruction in the airways that lead to each lung.

Those of skill in the art will appreciate that the management of bodily airways is not limited to those devices enabling respiration, but rather may extend to the panoply of devices relating to diseases of the larynx, pharynx, or nasal passages.

A laryngectomy is one procedure that implicates airway management devices. A patient may undergo a laryngectomy in response to cancer of the larynx or possibly because of trauma to the region. A total laryngectomy will have profound effects on the patient. In a total laryngectomy, the larynx is surgically separated from the mouth, nose and esophagus, and the entire larynx, including the vocal chords, is removed. The patient must thereafter use a laryngectomy tube for breathing. Further, due to the separation and lack of vocal chords, a patient may initially be unable to speak.

Some airway management devices are non-respiratory in the sense that they do not enable breathing directly, but still are related to the respiratory system generally. In healthy individuals, the larynx is instrumental for speech, but for laryngectomicized individuals speech is still possible through alternative methods using speech prosthetic devices. Voice button devices, such as a "Panje" voice button and a "Groningen" voice button, help restore speech by allowing air, but not fluids, through an artificial fistula formed between the larynx and the esophagus.

Other non-respiratory airway management devices include salivary bypass tubes and esophageal tubes. Laryngectomies may create salivary fistulas which are problematic if formed over the laryngectomy stoma. This detrimental post-laryngectomy effect can be treated by using a salivary bypass tube. Also, following a laryngoesophagectomy, an esophageal tube may be used to bridge the gap between the pharyngostome and esophagostome.

Another example of a condition that may necessitate an airway management device is laryngeal stenosis. Laryngeal stenosis may occur if a patient has been intubated for a prolonged period of time. One device used in its treatment is a laryngeal umbrella keel. Laryngeal umbrella keels are sometimes used before removing a laryngeal stent, to insure reformation of a sharp anterior commissure and to prevent formation of an anterior web.

Nasal splints are often used to relieve obstructions in the nasal cavity. Obstructions may occur, for example, following surgery of the nasal cavity and paranasal sinuses, which often results in the mucosal lining the nasal cavity becoming raw and rough and to form scars. They are inserted after nasal surgery on turbinates, the polyps (polypectomy), the septum (septoplasty), and after sinus surgery. The splints offer an airway (if the design incorporates a lumen, or tube); reduce, prevent or treat, the occurrence of synechiae formation (granulation); prevent adhesions of tissues or membranes within the nasal cavity; and control bleeding.

However, all of these devices suffer from several drawbacks. Airway management devices are often plagued by granulation, crusting and mucus build up. Further, such devices run the risk of compromising bodily walls and can be difficult for the patient to clean and maintain. In addition, ease of insertion and removal of complementary devices such as tubes can be hampered by the build up or encrustation of bodily fluids or by device fit friction. At the same time, however, another problem with airway management devices is the possibility of becoming accidentally dislodged. Thus there is a need for airway management devices which prevent build up of mucus, encrustation, or bodily fluids, yet remain firmly implanted in the patient with little likelihood of becoming accidentally dislodged. The present invention is directed towards a device solving these and other problems associated with the known devices.

SUMMARY OF THE INVENTION

One aspect of the present invention is directed to an airway management device including a tube with a lumen extending therethrough and with the tube having an inner and outer surface. The outer surface and inner surface of the tube have a protective polymeric coating.

An aspect of the invention is directed to an inner cannula for use with an airway management device such as a tracheostomy tube. The inner cannula may comprise an open distal end, an open proximal end that extends, a lumen extending therebetween having an inner surface, and an outer surface. Between the distal and proximal ends, the inner cannula may comprise a general curvature. In some embodiments, the inner cannula comprises a protective coat that covers one or more portions of the outer surface and/or inner surface of the stent. In certain embodiments, the coating is a polymeric coating, such as parylene.

Another aspect of the present invention is directed to a stoma stent system including a tube with a lumen extending therethrough, an exterior flange formed on the proximal end of the tube, and a tracheal flange formed on the distal end of the tube. The tube fluidly connects the exterior flange to the tracheal flange. The exterior flange and the tracheal flange have a protective polymeric coating.

A still further aspect of the present invention is directed to a voice prosthesis device including a voice button with a lumen extending therethrough, a tracheal flange attached to a tracheal end of the voice button and an esophageal flange attached to the esophageal end of the voice button. The inner surface of the voice button, the tracheal flange, and the esophageal flange are coated with a protective polymeric coating.

Yet another aspect of the present invention relates to a bronchial stent having a generally tubular shape. In certain embodiments, the stent may comprise an open distal end, an open proximal end, a lumen extending therebetween having an inner surface, an outer surface, and a longitudinal axis through the center of the lumen. In certain embodiments, the bronchial stent may comprise a means to prevent movement or displacement of the stent, and may further comprise a protective coating that covers one or more portions of the outer surface or inner surface of the stent.

In certain embodiments, the means to prevent movement or displacement of the stent may be one or more rings around the circumference of the stent, or the like. These rings may be located on the distal end of the stent, on the proximal end of the stent, in the middle of the stent, or any combination thereof.

In other embodiments, the means to prevent movement or displacement of the stent may be one or more posts that extend outwardly from the outer surface of the stent, or the like. The posts may be cylindrical, cubic, pyramidal, or prism-shaped. Also, the posts may be distributed randomly or in a pattern along the outer surface of the stent.

In certain embodiments, the means to prevent movement or displacement may be both rings and posts.

The protective coating on the bronchial stent may be a polymeric coating. The polymer may be parylene.

In certain embodiments, the distal end of the bronchial stent bifurcates into a first tubular diagonal arm and a second tubular diagonal arm, wherein each arm comprises an open distal end, an open proximal end, a lumen therebetween having an inner surface, an outer surface, and a longitudinal axis through the center of the lumen of each diagonal arm. In some embodiments, the lumen in the tubular diagonal arms is continuous with the lumen of the stent. In certain embodiments, the lengths of the first tubular diagonal arm and the second tubular diagonal arm may be equal or unequal.

In further embodiments, the longitudinal axis of the bronchial stent forms a first angle with the longitudinal axis of the first tubular diagonal arm and the longitudinal axis of the bronchial stent forms a second angle with the longitudinal axis of the second tubular diagonal arm. In some embodiments, the first angle and the second angle are equal or unequal.

In certain embodiments, the bronchial stent further comprises a third tubular arm extending from the stent wherein the third tubular arm comprises a first open end, a second open end, a lumen extending therebetween having an inner surface, an outer surface, and a longitudinal axis through the center of the lumen of the third tubular diagonal arm.

A further aspect of the present invention is directed to a nasal splint. In some embodiments, the nasal splint comprises an oblong-shaped base comprising a first curved end, a second curved end, and a middle region therebetween wherein middle region comprises a first edge, a second edge, a first surface, a second surface, and a protective coating that covers one or more portions of the first surface and/or second surface, of the splint.

In some embodiments, the protective coating may be a polymeric coating. In certain embodiments, the polymer is parylene.

In certain embodiments, the first edge of the middle region may be curved or substantially straight. In some embodiments, the first edge of the middle region may further comprise a portion, which resembles the shape of a shark's dorsa fin, extending from the first edge. In further embodiments, the second edge of the middle region is curved or substantially straight.

In further embodiments, the nasal splint may further comprise tubular structure on the first surface of the base, wherein the tubular structure extends between the first end of the base and the second end of the base, and wherein the tubular structure comprises: (i) a first open end; (ii) a second open end; (iii) a lumen extending therethrough having an inner surface and an inner circumference; (iv) an outer surface; (v) an outer circumference; and (vi) a tubular wall between the inner surface and outer surface.

In certain embodiments, the tubular structure may be adjacent to the first edge of the middle region of the base, the second edge of the middle region of the base, or is in the center of the base. In some embodiments, the first end of the tubular structure and the second end of the tubular structure are curved, and/or the tubular structure between the first and the second end is curved.

In some embodiments, nasal splint may further comprise a protective coating that covers one or more portions of the inner surface, outer surface, or both the inner surface and outer surface, of the splint. In certain embodiments, the protective coating is a polymeric coating. In further embodiments, the polymer is parylene.

In certain embodiments, nasal stent may further comprise a substantially flat segment that extends from the tube and is parallel to the base.

While certain designs of nasal splints are described herein, embodiments of the present invention are also directed to other nasal splint designs known in the art, wherein the nasal splints comprise a protective coating on one or more portions of the splint surfaces.

The various features of novelty which characterize the invention are pointed out in particularity in the claims annexed to and forming a part of this disclosure. For a better understanding of the invention, its operating advantages and specific objects attained by its uses, reference is made to the accompanying descriptive matter in which preferred embodiments of the invention are illustrated.

BRIEF DESCRIPTION OF THE DRAWINGS

For a more complete understanding of the invention, reference is made to the following description and accompanying drawings, in which:

FIG. 1 is a side view of a tracheostomy tube according to one aspect of the present invention;

FIG. 2 is a cut away view of a tracheostomy tube according to one aspect of the present invention;

FIG. 3 is a front view of a tracheostomy tube according to one aspect of the present invention;

FIG. 4 is a front view of a stoma stent according to one aspect of the present invention;

FIG. 5 is a cut away view of a stoma stent according to one aspect of the present invention;

FIG. 6 is a side view of a stoma stent according to one aspect of the present invention;

FIG. 7 is a side view of a T-tube according to one aspect of the present invention;

FIG. 8 is a cut away view of a T-tube according to one aspect of the present invention;

FIG. 9 is a front view of a T-tube according to one aspect of the present invention;

FIG. 10 is a front view of a transtracheal oxygen stent according to one aspect of the present invention;

FIG. 11 is a top view of a transtracheal oxygen stent according to one aspect of the present invention;

FIG. 12 is a cut away side view of a transtracheal oxygen stent according to one aspect of the present invention;

FIG. 13 is a side view of an oxygen delivery system for the transtracheal oxygen stent according to one aspect of the present invention;

FIG. 14 is a side view of a laryngectomy tube according to one aspect of the present invention;

FIG. 15 is a cut away view of a laryngectomy tube according to one aspect of the present invention;

FIG. 16 is a front view of a laryngectomy tube according to one aspect of the present invention;

FIG. 17 is a side view of a Panje voice button according to one aspect of the present invention;

FIG. 18 is a top view of a Panje voice button according to one aspect of the present invention;

FIG. 19 is a cut away view of a Panje voice button according to one aspect of the present invention;

FIG. 20 is a side view of a Groningen voice button according to one aspect of the present invention;

FIG. 21 is a cut away view of a Groningen voice button according to one aspect of the present invention;

FIG. 22 is a top view of a Groningen voice button according to one aspect of the present invention;

FIG. 23 is a side view of a salivary bypass tube according to one aspect of the present invention;

FIG. 24 is a cut away view of a salivary bypass tube according to one aspect of the present invention;

FIG. 25 is an end view of a salivary bypass tube according to one aspect of the present invention;

FIG. 26 is a front view of a laryngeal umbrella keel according to one aspect of the present invention;

FIG. 27 is a side view of a laryngeal umbrella keel according to one aspect of the present invention;

FIG. 28 is a top view of a laryngeal umbrella keel according to one aspect of the present invention;

FIG. 31 is a side view of a bronchial stent comprising rings according to one aspect of the present invention;

FIG. 32 is a cut-away side view of a bronchial stent comprising rings according to one aspect of the present invention;

FIG. 33 is a side view of a bronchial stent comprising posts according to one aspect of the present invention;

FIG. 35 is a cut-away side view of a bronchial stent comprising posts according to one aspect of the present invention;

FIG. 43 is a side view of a nasal splint according to one aspect of the present invention;

FIG. 46 is an end view of a nasal splint comprising a segment extending from the tubular structure of the splint according to one aspect of the present invention;

FIG. 48 is a side view of a nasal splint comprising a portion that resembles the shape of a shark's dorsal fin extending from the first edge according to one aspect of the present invention.

FIG. 53 is a cut-away bottom view of a Tellez Nasal Splint according to one aspect of the present invention;

FIG. 55 is an end view of a Doyle Shark Nasal Splint according to one aspect of the present invention;

DESCRIPTION OF THE INVENTION

Figure 29:
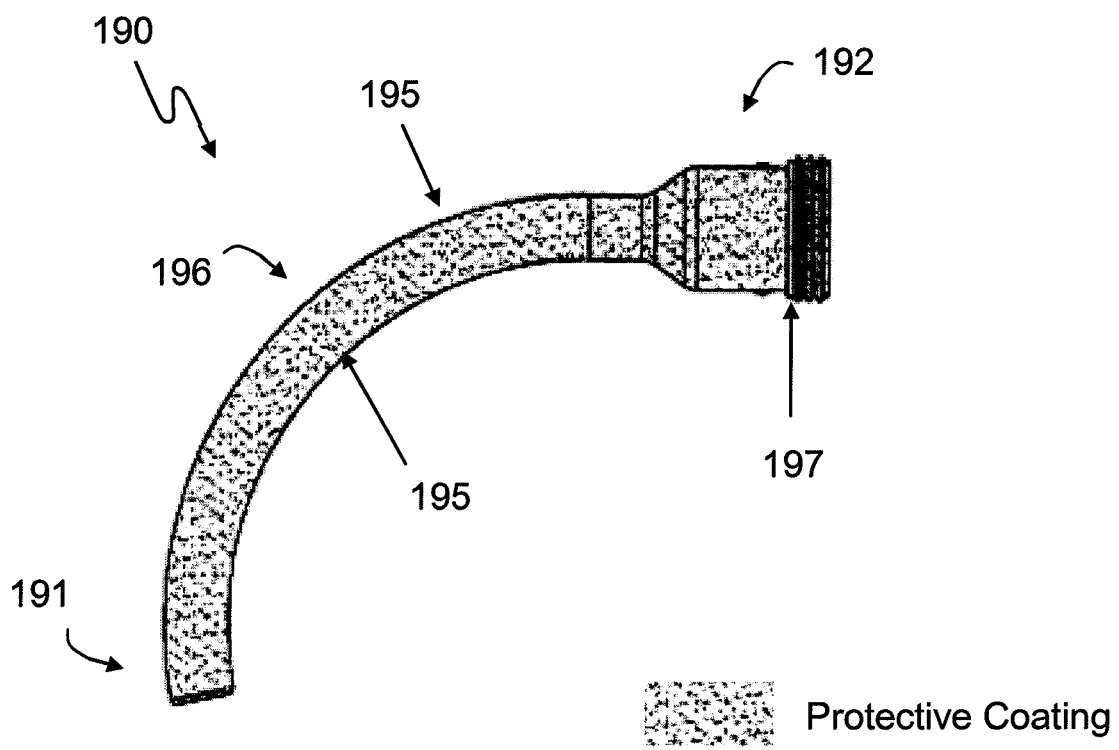
FIG. 29 is a side view of an inner cannula according to one aspect of the present invention.

The present invention overcomes the shortcomings of the prior art by coating airway management devices with a protective polymeric coating. One suitable type of polymer is parylene. Parylene is the name for a series of polymers based on the monomer, para-xylene (p-xylene), or 1,4 dimethyl-benzene. There are three commercially available variations of parylene that display differences at the monomeric level: parylene N, parylene C, and parylene D. In one preferred embodiment, the instant invention uses parylene N or parylene C. Parylene is applied in a thickness of about 0.00003" to 0.0001" and more preferably in a thickness of about 0.00005".

The backbone of the parylene polymer is made entirely of carbon and thereby is not vulnerable to hydrolytic breakdown in an aqueous environment. Parylene also has excellent properties as a film lubricant and its coefficient of friction approaches TEFLON®. Also, with a dielectric constant relatively independent of frequency and temperature, parylene also is an excellent electric insulator.

The devices contemplated by the present invention can be formed using any number of materials conventional to those skilled in the art for airway management devices. For example, one preferable material is medical grade silicone but other materials such as polyvinylchloride (PVC) could also be used without departing from the scope of the present invention.

One embodiment of the present invention is a protectively coated tracheostomy tube as shown in FIGS. 1-3. Areas with a protective polymeric coating are illustrated by the shaded regions. FIG. 1 is a side view of a tracheostomy tube 10. The tube 10 is open at the distal end 18 and the proximal end 20. Tube 10 has an outer surface 12 and a lumen 16 extending therethrough having an inner surface 14. A neck plate 22 is attached at the proximal end 20, which in use rests against a patient's neck. One embodiment of the invention contemplates coating both the outer surface 12 of the tube 10 with a protective polymeric coating, as depicted in FIGS. 1 and 3, as well as and the inner surface 14 of the lumen 16, as depicted in FIG. 2. Coating the tracheostomy tube 10 in this manner serves to control mucus and granulation accumulation both internally and externally. In addition, such coating serves to ease in the insertion and removal of suction tubes. The neck plate 22 is preferably not coated with the polymeric protective coating.

Figure 30:
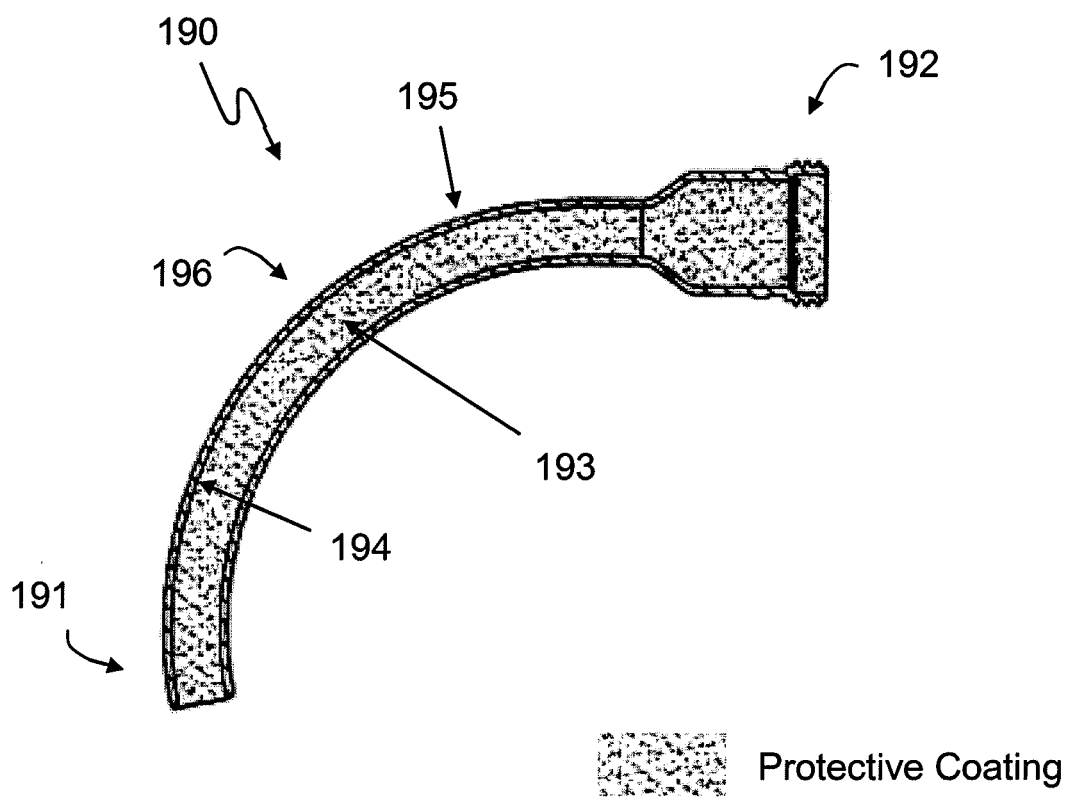
FIG. 30 is a cut-away side view of an inner cannula according to one aspect of the present invention.

Those of skill in the art will appreciate that an inner cannula may be inserted to the lumen 16 of the tube 10. FIGS. 29 and 30 depict an inner cannula 190 in accordance with an embodiment of the invention. The inner cannula 190 may comprise an open distal end 191, an open proximal end 192, and a lumen 193 extending therebetween having an inner surface 194, and an outer surface 195. Between the distal end 191 and the proximal end 192, the inner cannula 190 may comprise a general curvature 196 which is designed to fit into the tracheostomy tube, e.g., to fit through the stoma and into the trachea of the patient. The inner cannula 190 may further comprise a sealing ring 197 on the proximal end 191, which prevents mucus from migrating into the area between the outside of the inner cannula 190 and the inside of the tracheostomy tube. The inner cannula can be made of a softer non-toxic plastic, rubber or silicone material.

The outer surface 195 and inner surface 194 (shown in the cut-away view of the inner cannula 190 in FIG. 30) of the inner cannula may be coated with the polymeric protective coating to ease insertion and prevent mucus build up or granulation.

FIGS. 4-6 show a stoma stent 24 in accordance with another embodiment of the present invention. Surrounding the proximal end 36 of the stoma stent 24 is an exterior flange 38 and surrounding the distal end 34 is a tracheal flange 40. The exterior flange 38 and the tracheal flange 40 are fluidly connected by a tube 26 with an outer surface 28 and with a lumen 25 extending therethrough and having an inner surface 30. The inner surface 30 has a portion 32 proximal to the tracheal flange 40 and a portion 60 proximal to the exterior flange 38.

The exterior flange 38 and the tracheal flange 40 are both coated with a protective coating. The outer surface 28 is not coated with a protective coating in order to prevent the stoma stent 24 from being coughed out of position. The inner surface 30 of the lumen 25 is coated with a protective polymeric material except for the portion 60 proximal to the exterior flange 38. The distal portion 60 is not coated. Coating the tracheal flange 40 with protective material prevents the accumulation of granulation, crusting and mucus. Further, the smoother surface reduces the possibility of compromising the tracheal wall of the patient. With regard to the exterior flange 38, the protective coating prevents the accumulation of granulation, crusting and mucus and allows for easier cleaning and maintenance of the stoma stent 24. The uncoated portion 60 provides enhanced friction to hold an item such as a cannula or a plug 48 firmly in the stoma stent.

As seen in FIGS. 4 and 6, also attached to the exterior flange 38 is a tether 46 connected to a plug 48. The plug 48 has a cylindrical inner wall 50 and a tapered outer wall 54 attached axially to a base 52, as shown in FIGS. 4 and 6. The tapered outer wall 54 has a portion 58 proximal to the base 52 and a portion 56 distal to the base 52. The distal portion 56 is not coated. The plug 48 is of a dimension and configuration to fit tightly within the lumen 30 of the tube 26 with base 52 abutting the exterior flange 38 and the uncoated portion 56 of the plug 48 secured to the uncoated portion 60 of the stoma stent 24.

Another embodiment of the invention is a polymer coated tracheal T-tube 62, as shown in FIGS. 7-9. FIG. 7 is a side view of a tracheal T-tube with a vertical arm 64 and a horizontal arm 66 arranged perpendicularly to the vertical arm 64 in a T shape. Joining the tube arms 64 and 66 forms a T-tube 62 having a single lumen 70 and one outer surface 68. Inner surface 72 is located within the vertical arm 64. Inner surface 74 is located within the horizontal arm 66. Inner surface 76 also is located within the horizontal arm 66 at a location distal to the vertical arm 64. The outer surface 68 of the T-tube 62 is coated with a protective material. Further, the inner surfaces 72 and 74 of the horizontal and vertical arms 66 and 64 are coated with a protective layer which allows for ease of insertion/removal of suction catheter, if necessary. However, the inner surface 76 of the horizontal arm 66 is not coated with a protective coating.

As shown by FIGS. 7 and 9, a tether 78 is attached to the horizontal arm 66 and connects a plug 80 to the horizontal arm 66. The plug 80 has a cylindrical wall 82 attached axially to a base 83 with a tapered outer wall 84, as shown in FIGS. 7 and 9. The tapered outer wall 84 has a proximal portion 86 and a distal portion 88 to the base 83. The plug 80 is of a dimension and configuration to fit tightly adjacent to the inner surface of the distal portion 76 of the horizontal arm 66 of the T-tube 62. Correspondingly, the distal portion 88 of the outer wall 84 of plug 80 is not coated ensuring a secure fit.

In yet another embodiment, FIGS. 10-12 show a transtracheal oxygen stent 90 coated with protective polymer. FIG. 11 shows a top view of a transtracheal oxygen stent 90 having a tube 92 with a lumen 102 extending therethrough having an inner surface 100. The tube 92, having an outer surface 98, is open at the proximal end 94 and the distal end 96. A tracheal flange 106 is attached at the distal end 96 of the tube 92 and an exterior flange 104 is attached at the proximal end 94, as shown in FIGS. 11 and 12. The tracheal flange 106 and the exterior flange 104 are both coated with a protective coating. Coating the tracheal flange 106 with protective material prevents the accumulation of granulation, crusting and mucus. Further, the smoother surface reduces the possibility of compromising the tracheal wall. With regard to the exterior flange 104, the protective coating prevents the accumulation of granulation, crusting and mucus and allows for easier cleaning and maintenance. What is more, as shown by FIG. 12, the inner surface 100 of the lumen 102 is coated with a protective coating. However, as shown by FIG. 11, the external surface 98 of the tube 92 does not have a coating. Coating the inner surface 100 with a protective material will prevent accumulation of crusting and mucus. The external surface 98 is not coated with a protective coating to prevent the stent 92 from being coughed out of the stoma formed in the patient.

In a further embodiment, the transtracheal oxygen stent 92, as shown in FIGS. 10-12 is adaptable for use with the oxygen delivery catheter 108 shown in FIG. 13 and is comprised of tubing 110 that connects the stent shown in FIGS. 19-21 to an oxygen source (not shown). The tubing 110 has a connecting portion 112 with an outer surface 114 that fits within the lumen 102 of the transtracheal oxygen stent 92, as shown in FIGS. 10-12. The outer surface 114 of the connecting portion 112 has a protective polymeric coating to ease insertion.

FIGS. 14-16 show another embodiment of the present invention, namely a laryngectomy tube 116 coated with a protective polymer. The laryngectomy tube 116 comprises a curved tube 118 with an outer surface 120. The tube 118 has a proximal end 128, a distal end 129 and a lumen 124 which extends therethrough having an inner surface 122. A neck plate 126 is attached at the proximal end 128 of the tube 118. The neck plate 126, outer surface 120 and inner surface 122 are all coated with the protective polymer.

Another embodiment of the invention is a protectively coated device for voice prosthesis. In one embodiment, shown in FIGS. 17-19, a voice button 130 has three segments: 134, 136, and 138, and a lumen 142 extending therethrough. The voice button 130 has an open tracheal end 144 and a valved 152 esophageal end 146. The entire inner surface 140 of the lumen 142 is protectively coated to prevent crusting and mucus. The first segment is the tracheal segment 134. The tracheal segment 134 includes a tracheal flange 148. The external surface 151 including the surface of the tracheal flange 148 of the tracheal segment 134 has a protective coating. Coating the tracheal flange 148 prevents granulation, crusting and mucus in the device as well as allowing for easier cleaning and maintenance. The second segment is the intrafistular segment 136. In use this segment rests in the fistula between the trachea and the esophagus. The lumen 142 extends between the tracheal flange 148 and the esophageal flange 150 and through the intrafistular segment 136. The external surface 132 of the intrafistular segment 136 is not protectively coated. The third segment is the esophageal segment 138, including the esophageal flange 150 to the esophageal end 146, which contains a valve system 152 that allows air to pass through the voice button 130 from the lungs but prevents fluids from the esophagus from passing in the opposite direction. The external surface 153 of the esophageal segment 138 is protectively coated. Similarly, the esophageal flange 150 has a protective coating to prevent granulation, crusting, and mucus accumulation. Coating the esophageal flange 150 will also prevent the accumulation of food particulates. Another embodiment may include a string 154 attached to the tracheal segment 134 that may be used to retrieve the device from the fistula. This string 154 may also be coated with a protective polymeric coating. One skilled in the art would know the device previously described as a "Panje voice button."

Another embodiment of the invention is a protectively coated voice button 158, as shown in FIGS. 20-22. In this embodiment, the voice button 158 has a lumen 160 extending therethrough having an inner surface 161. The voice button 158 has an open tracheal end 168 and an esophageal end 170 with a valve 172. The tracheal end 168 includes a tracheal flange 164 and the esophageal end 170 includes an esophageal flange 166. The entire inner surface 161 of the lumen 160 is coated by a protective coating, however, the external surface 162 of the voice button 158 is not coated. The tracheal flange 164 is coated with a protective coating as is the esophageal flange 166. The valve 172 allows air to pass through the voice button 158 from the lungs but prevents fluids from the esophagus to pass in the opposite direction. Another embodiment includes a string 174 attached to the laryngeal flange 164 to retrieve the device 156 from the fistula. In one embodiment, the string 174 is also coated with a protective coating. One skilled in the art would know the device previously described as a "Groningen voice button."

Yet another embodiment the present invention is a non-respiratory airway management device such as the salivary bypass tube 176 shown in FIG. 23-25. According to the present invention, the salivary bypass tube 176 has an exterior surface 182 and a lumen 180 which extends therethrough. The inner surface 178 of the lumen 180 is coated with a protective polymeric coating. However, the exterior surface 182 of the tube 176 is not coated with a protective polymeric coating. In one embodiment of the invention, the tube 176, having proximal 175 and distal 177 ends, further comprises a funnel 179 attached to the proximal end 175. The inner surface 181 of the funnel 179 has a protective polymeric coating but the outer surface 183 of the funnel 179 is not so coated.

A further embodiment of the present invention is a non-respiratory airway management device such as the laryngeal umbrella keel 184 shown in FIGS. 26-28. The laryngeal umbrella keel 184 is comprised of an umbrella-like extralaryngeal cover 186 and a thin intralaryngeal insert 188, joined perpendicularly in a T-shape. The umbrella-like extralaryngeal cover 186 is not coated with a protective polymer. The thin intralaryngeal insert 188 is protectively coated. Coating the thin intralaryngeal cover 188 prevents the formation of granulation and eases removal of the device, thereby reducing the possibilities of vocal chord adhesions.

Yet another embodiment of the present invention relates to a bronchial stent system, such as the bronchial stent shown in FIGS. 31-35. Areas with a protective polymeric coating are illustrated by the shaded regions. The stent 200 may be tubular in shape, and comprise an open distal end 201 and an open proximal end 202. The stent may also comprise a lumen 203 extending between the distal end 201 and the proximal end 202, such that the lumen 203 comprises an inner surface 204, an outer surface 205, and a longitudinal axis 206 through the center of the lumen. The lumen 203 and the inner surface 204 are shown in the cut away side view of the bronchial stent in FIG. 32.

The bronchial stent 200 may further comprise a means to prevent movement or displacement of the stent during use. Means to prevent movement or displacement may comprise one or more rings around the circumference of the stent, one or more posts or protrusions that extend from the outer surface of the stent, or the like. For example, the embodiment depicted in FIGS. 31 and 32 demonstrate a bronchial stent 200 comprising rings 207 as a means to prevent movement or displacement of the stent. The rings 207 may be located at the distal end 201, the proximal end 202, any site therebetween, or any combination thereof. In the embodiment shown in FIGS. 31 and 32, the rings 207 are located at the distal end 201 and proximal end 202.

Figure 34:
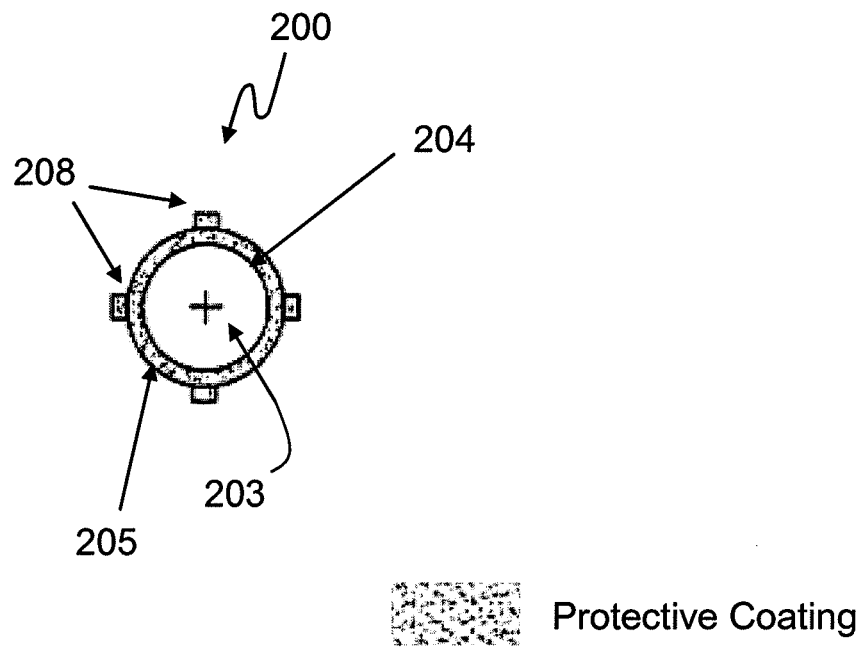
FIG. 34 is an end view of a bronchial stent comprising posts according to one aspect of the present invention.

Another example of means to prevent displacement or movement of the bronchial stent 200 may be posts, or protrusions, which extend radially from the surface of the stent. For instance, FIGS. 33-35 depict a bronchial stent 200 comprising posts 208 shown in a side view (FIG. 33), in a cross-sectional view (FIG. 34), and in a cut-away side view (FIG. 35). The posts 208 can be of any shape or form, including cubic posts, cylindrical posts, pyramidal posts, and other prism-shaped posts. The posts may be distributed evenly or unevenly around the circumference of the bronchial stent, and there may be one or more rows of posts. In the embodiments depicted in FIGS. 33-35, the posts are in four rows distributed evenly around the circumference of the bronchial stent.

The bronchial stent may additionally comprise a coating on one or more portions of the inner surface 204, the outer surface 205, or both the inner surface 204 and outer surface 205. Coating the bronchial tube 200 in this manner serves to control mucus and granulation accumulation both internally and externally, as well as prevent adhesion to tissues which can cause bleeding upon removal, and prevent build-up of blood, or blood clots, to the stent. In certain embodiments, the entire inner surface 204 or outer surface 205, or both, may be coated.

The bronchial stent may further comprise a bifurcation on the distal end of the bronchial stent to form a bronchial Y-tube 210, as shown in FIGS. 36-39. The distal end may bifurcate into a first tubular diagonal arm 211 and a second tubular diagonal arm 221. The first tubular diagonal arm 211 may comprise an open distal end 212 and an open proximal end 213. The first tubular diagonal arm 211 may also comprise a lumen 214 extending between the distal end 212 and the proximal end 213 and having an inner surface 215, an outer surface 216, and a longitudinal axis 217 through the center of the lumen 214. The second tubular diagonal arm 221 may comprise an open distal end 222 and an open proximal end 223. The second first tubular diagonal arm 221 may also comprise a lumen 224 extending between the distal end 222 and the proximal end 223 and having an inner surface 225, an outer surface 226, and a longitudinal axis 227 through the center of the lumen 224. The lumen 214 in the first diagonal arm 211 and the lumen 224 in the second diagonal arm 221 may be continuous with the lumen 203 of the stent 200.

The lengths of the first diagonal arm 211 and the second diagonal arm 221 may be equal or unequal. Referring to the location of the diagonal arms around the circumference of the stent, the first tubular diagonal arm 211 and the second tubular diagonal arm 221 may be 180° apart around the circumference. In some embodiments, the first tubular diagonal arm 211 and the second tubular diagonal arm 221 may be between 0° and 180°, or between 45° and 135° or about 90° apart around the circumference.

The longitudinal axis 206 of the bronchial stent 200 may form a first angle 218 with the longitudinal axis 217 of the first tubular diagonal arm. The longitudinal axis 206 of the stent 200 may form a second angle 228 with the longitudinal axis 227 of the second tubular diagonal arm 221. The first angle 218 and the second angle 219 may be between 0° and 90°, or between 15° and 75° or between 30° and 60°. The first angle 218 may be the equal or unequal to the second angle 228.

The bronchial Y-tube may also comprise a coating on one or more portions of the inner surface, outer surface, or both, as described above.

Figure 38:
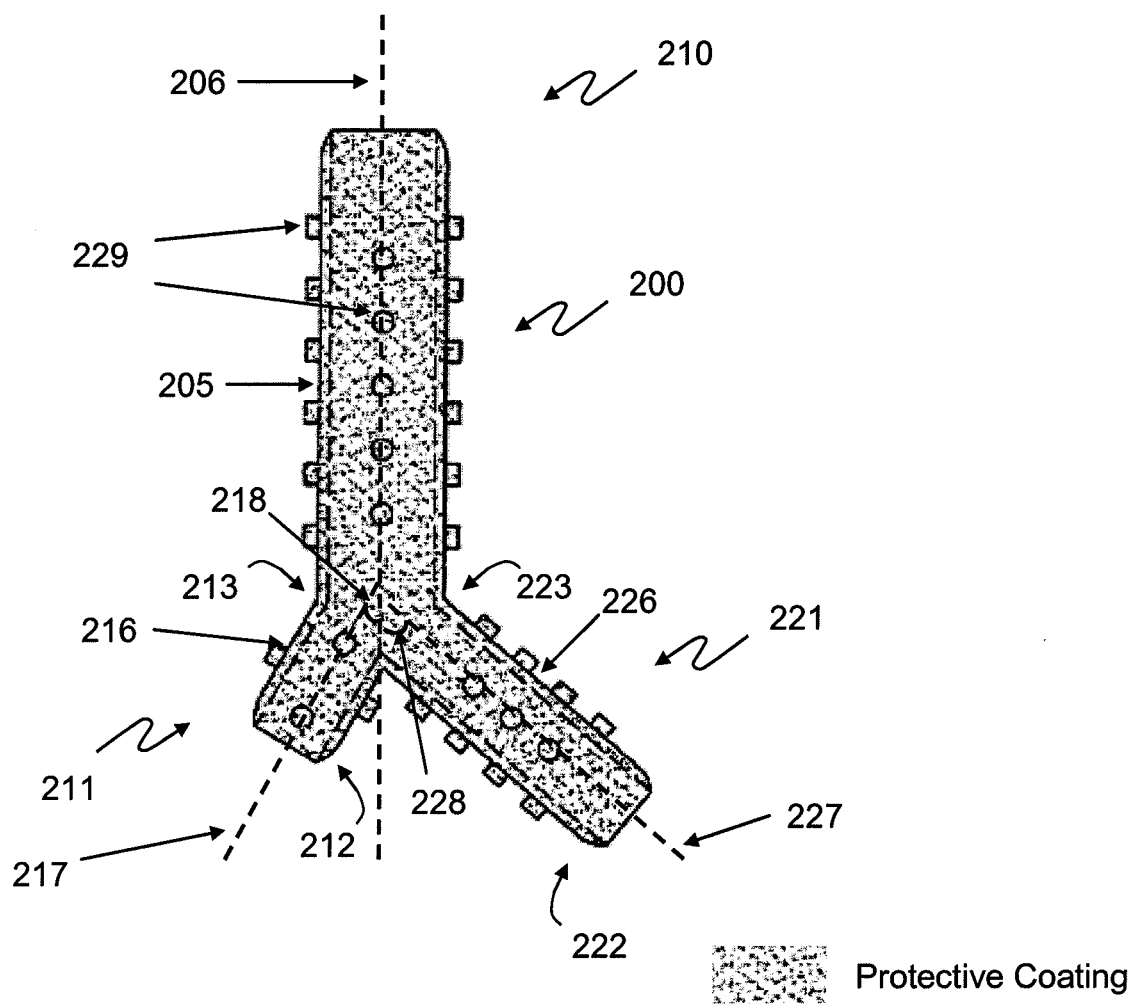
FIG. 38 is a side view of a bronchial Y-tube comprising posts according to one aspect of the present invention.
Figure 39:
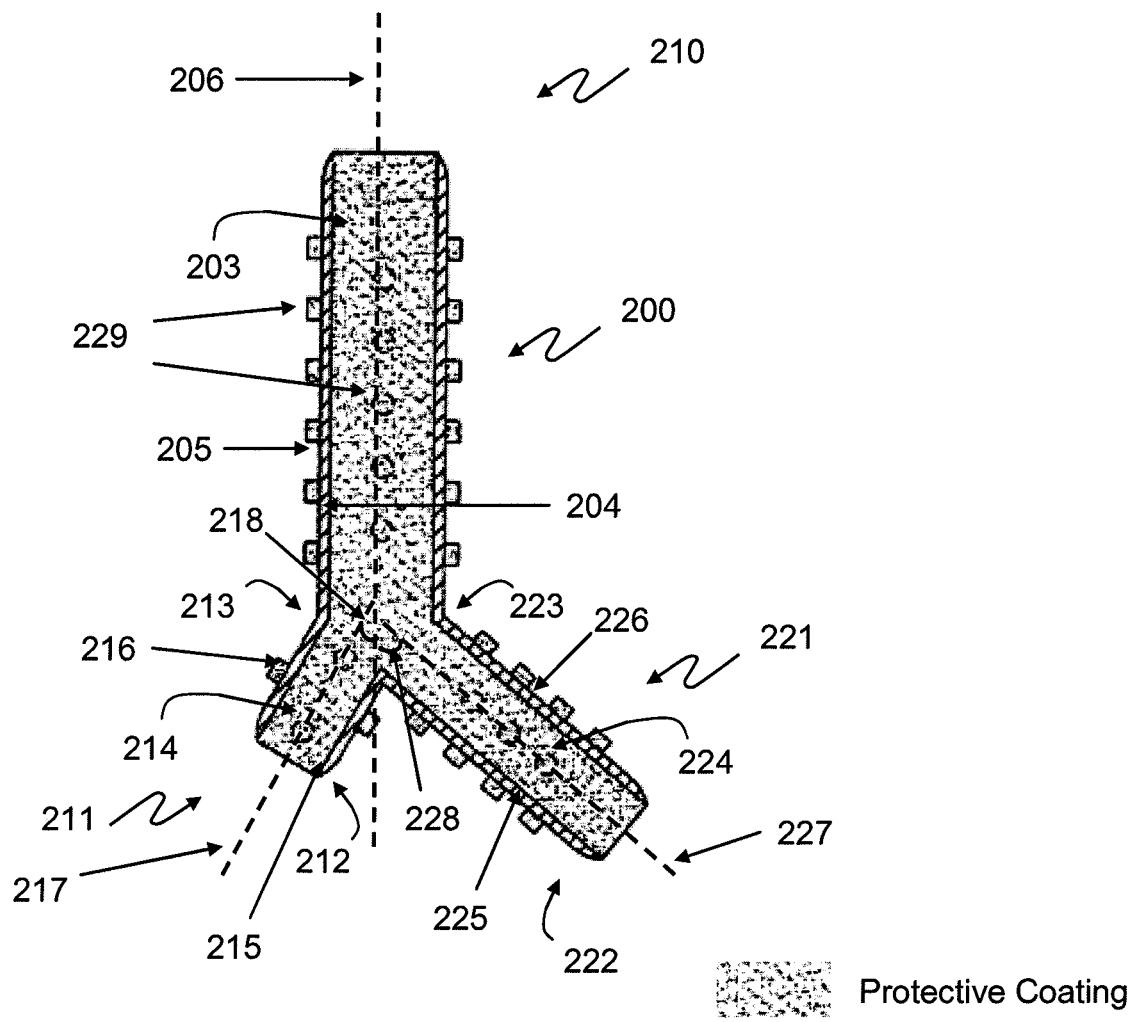
FIG. 39 is a cut-away side view of a bronchial Y-tube comprising posts according to one aspect of the present invention.

The bronchial Y-tube may further comprise means for preventing displacement or movement as described above. For example, FIGS. 38 and 39 depict the bronchial Y-tube having posts 229 as a means for preventing movement or displacement.

The bronchial stent 200 or the bronchial y-tube 210 may further comprise one or more tubular arms extending from the stent. FIGS. 40-43 depict an embodiment wherein a bronchial Y-tube comprises a third tubular arm 231 extending to form a bronchial TY-tube 230. The third tubular arm 231 may comprise a first open end 232 and a second open end 233. The third tubular arm 231 may also comprise a lumen 234 extending between the first open end 232 and the second open end 233 and having an inner surface 235, an outer surface 236, and a longitudinal axis 237 through the center of the lumen 234. The lumen 234 in the third tubular arm 231 may be continuous with the lumen 203 of the stent 200.

The longitudinal axis 206 of the bronchial stent 200 may form a third angle 238 with the longitudinal axis 237 of the third arm. The angle 238 may be between 0° and 180°, or between 45° and 135° or about 90°.

Referring to the location of the third tubular arm 231 around the circumference of the stent, the third tubular arm 231 may be aligned with either of the tubular diagonal arms 211 or 221, or may be unaligned with either tubular diagonal arm 211 or 221 and may be between 0° and 180° apart around the circumference from either tubular diagonal arm 211 or 221. If there is more than one tubular arm extending from the bronchial stent, these additional arms may aligned or unaligned with the tubular diagonal arms 211 and 221. Further, these addition arms may at the same site along the length of the bronchial stent or they may be at different sites.

The bronchial TY-tube may also comprise a coating on one or more portions of the inner surface, outer surface, or both, as described above.

The bronchial TY-tube may further comprise means for preventing displacement or movement, such as rings or posts or the like, as described above.

In the bronchial stent embodiments of the present invention, including the bronchial tubes, e.g., bronchial Y-tube, bronchial TY-tube, etc., the open distal and open proximal ends of the tube may be feathered outwardly or inwardly to facilitate its use within the airways.

Therefore, FIGS. 31-42 depict various embodiments of bronchial stent, bronchial Y-tube, and bronchial TY-tube. For example, FIGS. 31 and 32 show a bronchial stent 200 comprising a protective coating on its outer surface 205 and inner surface 204, and rings 207 on the distal end 201 and proximal end 202 as a means to prevent movement or displacement of the stent 200.

FIGS. 33 and 35 show a bronchial stent 200 comprising a protective coating on its outer surface 205 and inner surface 204, and posts 208 along the outer surface 205 of the stent 200.

Figure 36:
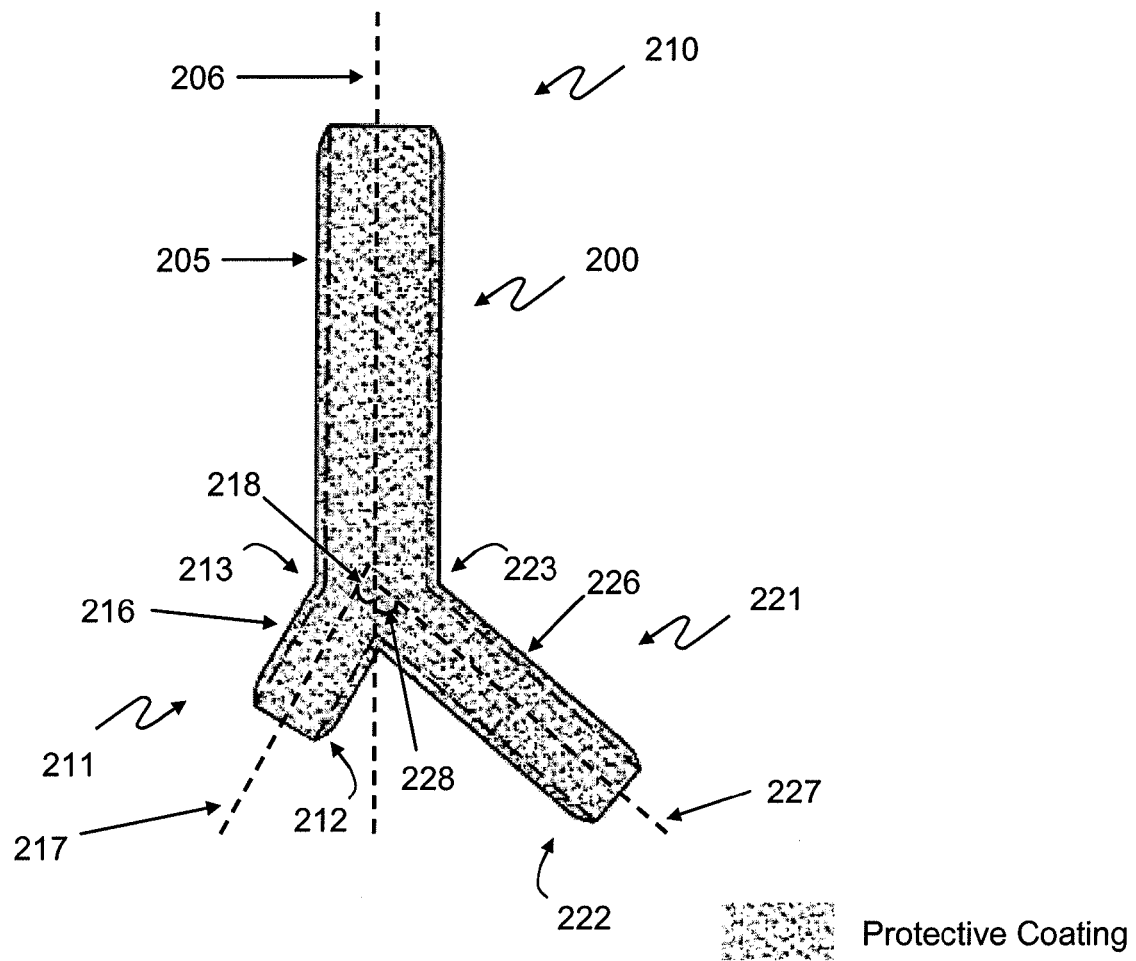
FIG. 36 is a side view of a bronchial Y-tube according to one aspect of the present invention.
Figure 37:
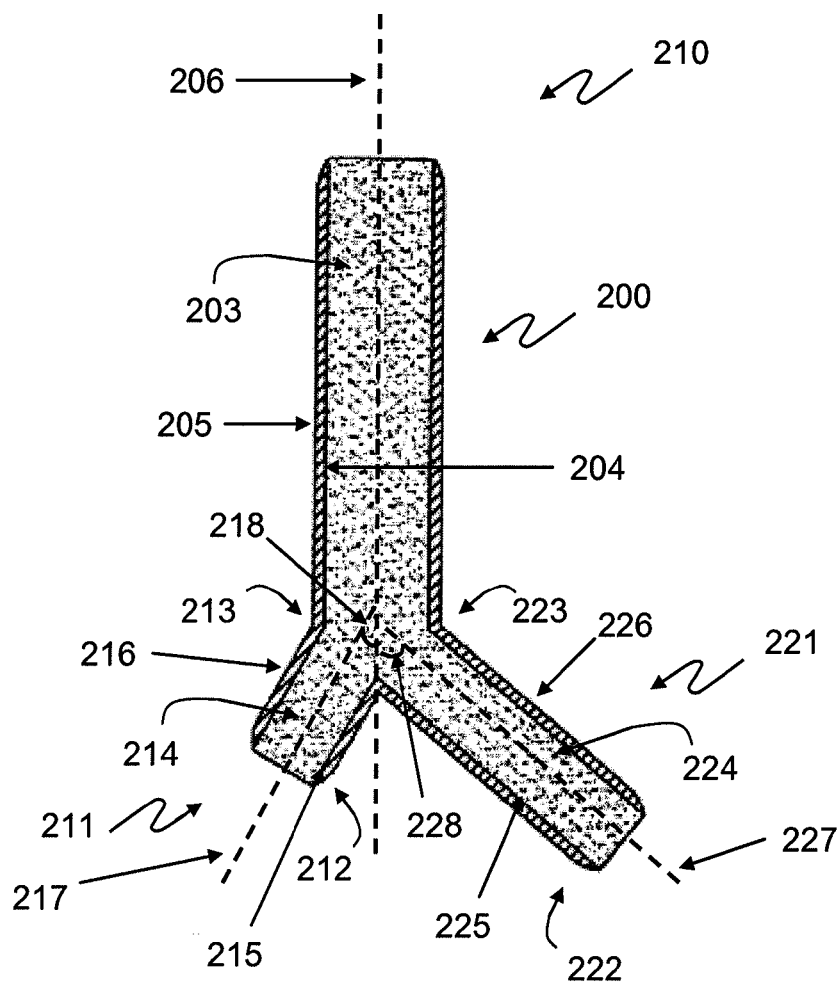
FIG. 37 is a cut-away side view of a bronchial Y-tube according to one aspect of the present invention.

FIGS. 36 and 37 show a bronchial Y-tube 210 comprising a bronchial stent 200 having a bifurcation, which comprises a first tubular diagonal arm 211 and a second tubular diagonal arm 221 which extends distally. The bronchial Y-tube also comprises a protective coating on the outer surfaces 205, 216 and 226, and inner surfaces 204, 215 and 225.

FIGS. 38 and 39 show a bronchial Y-tube 210 comprising a bronchial stent 200 having a bifurcation, which comprises a first tubular diagonal arm 211 and a second tubular diagonal arm 221 which extends distally. The bronchial y-tube also comprises a protective coating on the outer surfaces 205, 216 and 226 and inner surfaces 204, 215 and 225, and posts 229 along the outer surfaces 216 and 226.

Figure 40:
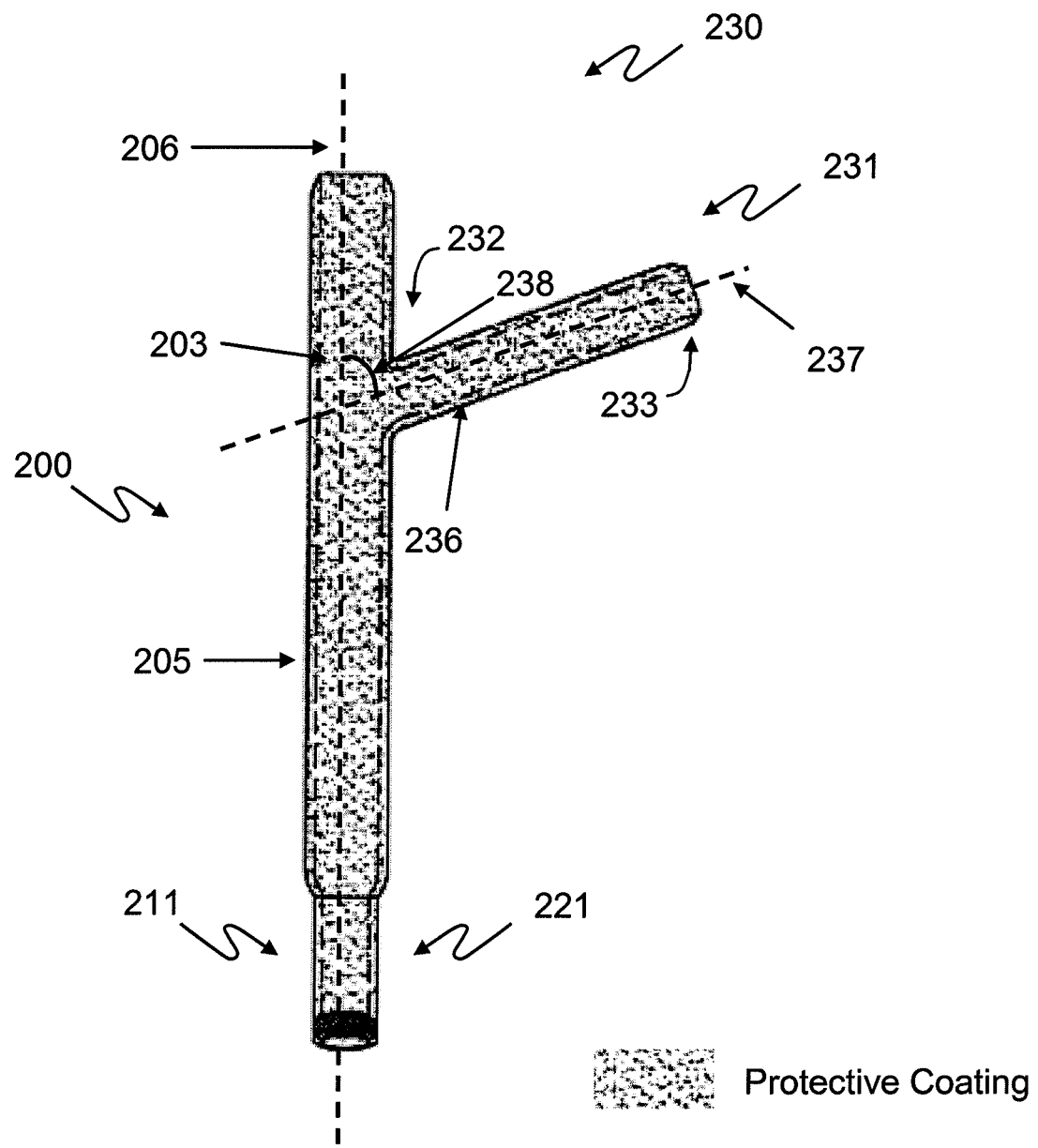
FIG. 40 is a side view of a bronchial TY-tube according to one aspect of the present invention.
Figure 41:
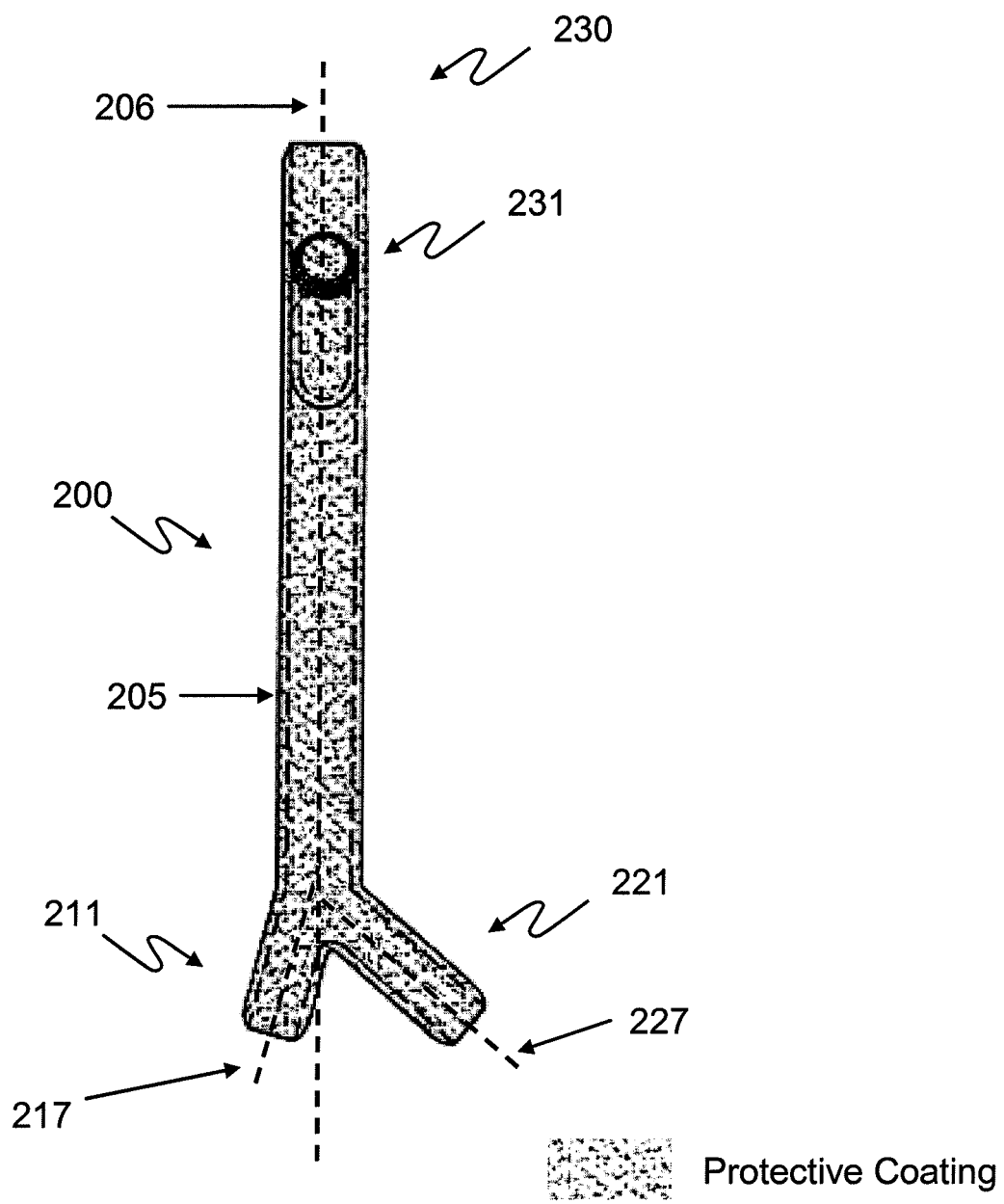
FIG. 41 is a second side view of a bronchial TY-tube according to one aspect of the present invention.
Figure 42:
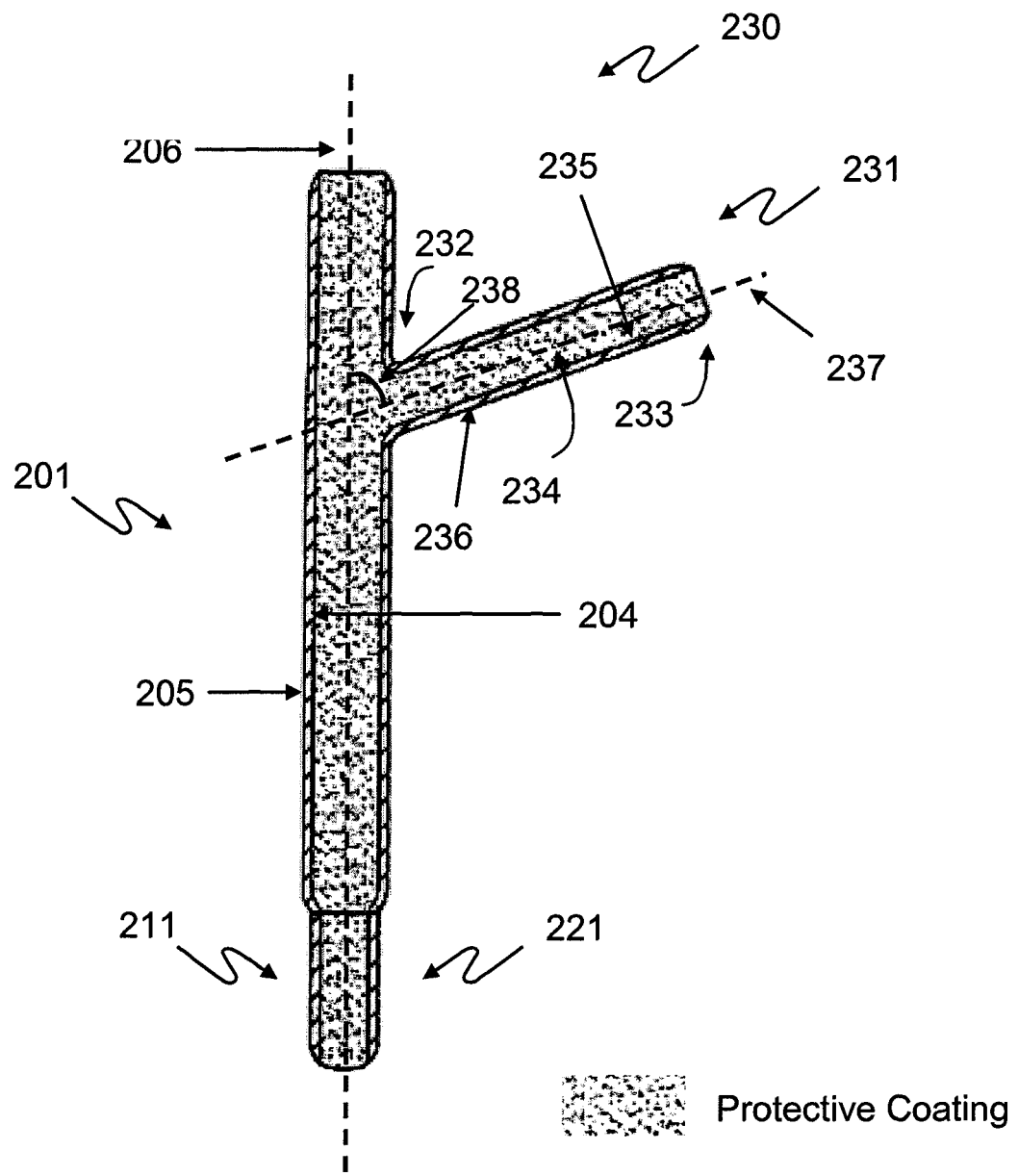
FIG. 42 is a cut-away side view of a bronchial TY-tube according to one aspect of the present invention.

FIGS. 40-42 show a bronchial TY-tube 230 comprising a bronchial stent 200 having a bifurcation comprising a first tubular diagonal arm 211 and a second tubular diagonal arm 221 which extends distally from the distal end of the stent 200, and a third tubular arm 231 extending from the stent 200. The bronchial TY-tube also comprises a protective coating on the outer surfaces 205, 216, 226, and 236, inner surfaces 204, 215, 225, and 235.

Figure 49:
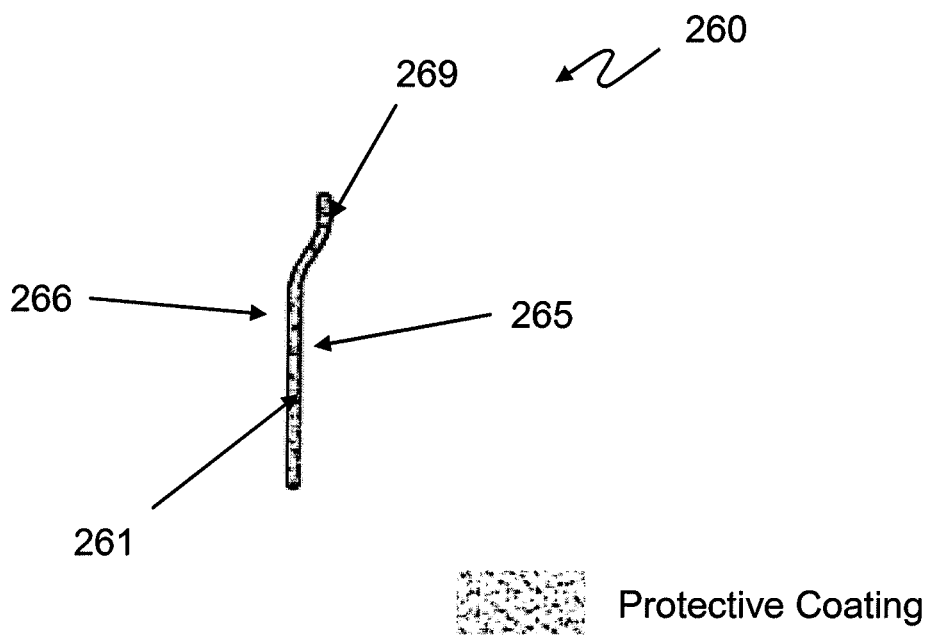
FIG. 49 is an end view of a nasal splint comprising a portion that resembles the shape of a shark's dorsal fin extending from first edge according to one aspect of the present invention.
Figure 50:
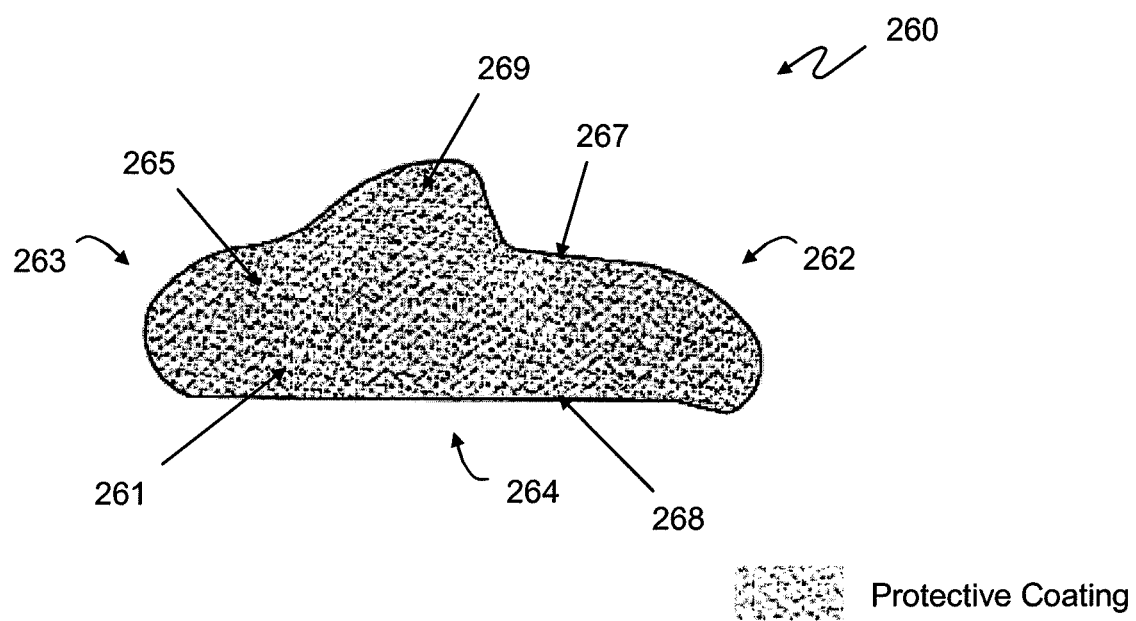
FIG. 50 is a second side view of a nasal splint comprising a portion that resembles the shape of a shark's dorsal fin extending from the first edge according to one aspect of the present invention.
Figure 54:
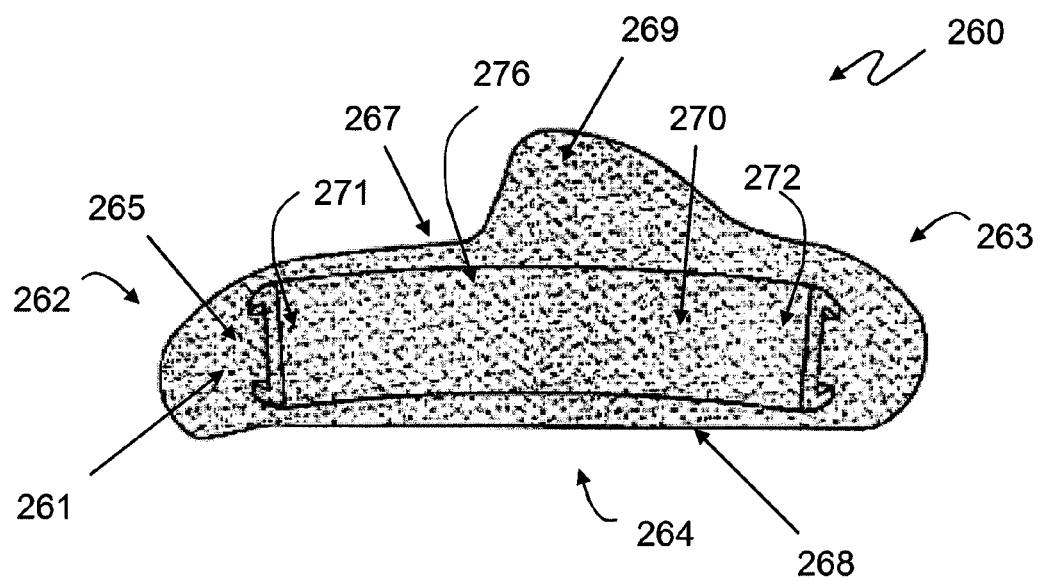
FIG. 54 is a side view of a Doyle Shark Nasal Splint according to one aspect of the present invention.

Another embodiment of the present invention relates to a nasal splint 260, such as the nasal splints shown in FIGS. 43-54, which represent different embodiments. The nasal splint 260 may comprise a base 261 comprising a first curved end 262, a second curved end 263, a middle region 264 extending therebetween, a first surface 265, and a second surface 266, such that the middle region comprises a first edge 267 and a second edge 268. The base 261 may be oblong in shape. The first edge 267 and the second edge 268 of the middle region 264 may be curved or substantially straight. The first edge 267 of the middle region 264 may alternatively comprise a portion that resembles the shape of a shark's dorsal fin, as depicted in FIGS. 48, 50, and 54.

The nasal splint 260 may further comprise a hole 269 near the first curved end 262, near the second curved end 263, or a combination thereof. The holes 269 are for purposes of suturing. The edge of the hole may be level with first surface 265 and/or the second surface 266, or the edge of the hole may comprise a lip. Also, the base 261 at the site of the holes may have a greater cross-section than other sites of the base 261. The holes 269 provide a secure feature that will allow the physician to pass a suture through, without tearing the silicone device. The suture aids in holding the splint in position.

Figure 51:
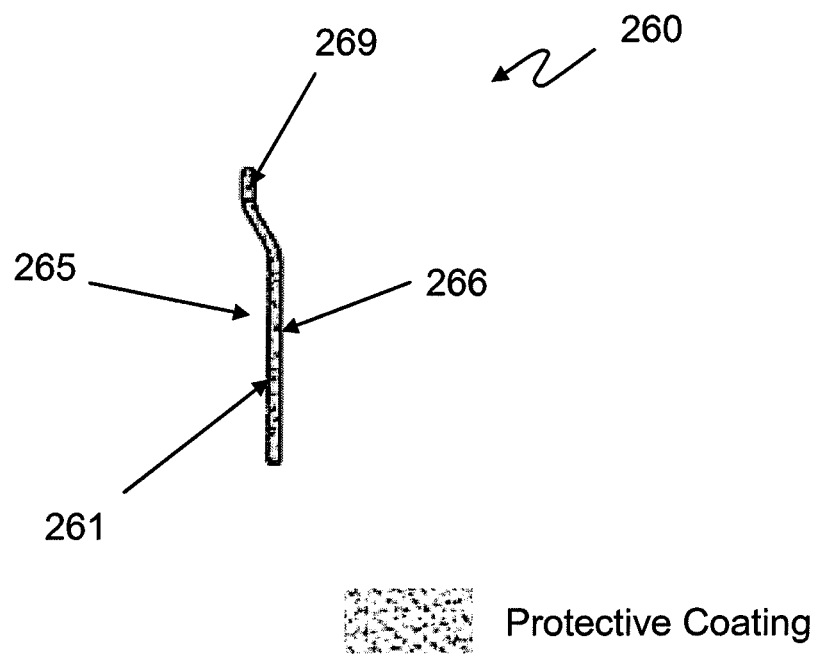
FIG. 51 is a second end view of a nasal splint comprising a portion that resembles the shape of a shark's dorsal fin extending from the first edge according to one aspect of the present invention.
Figure 56:
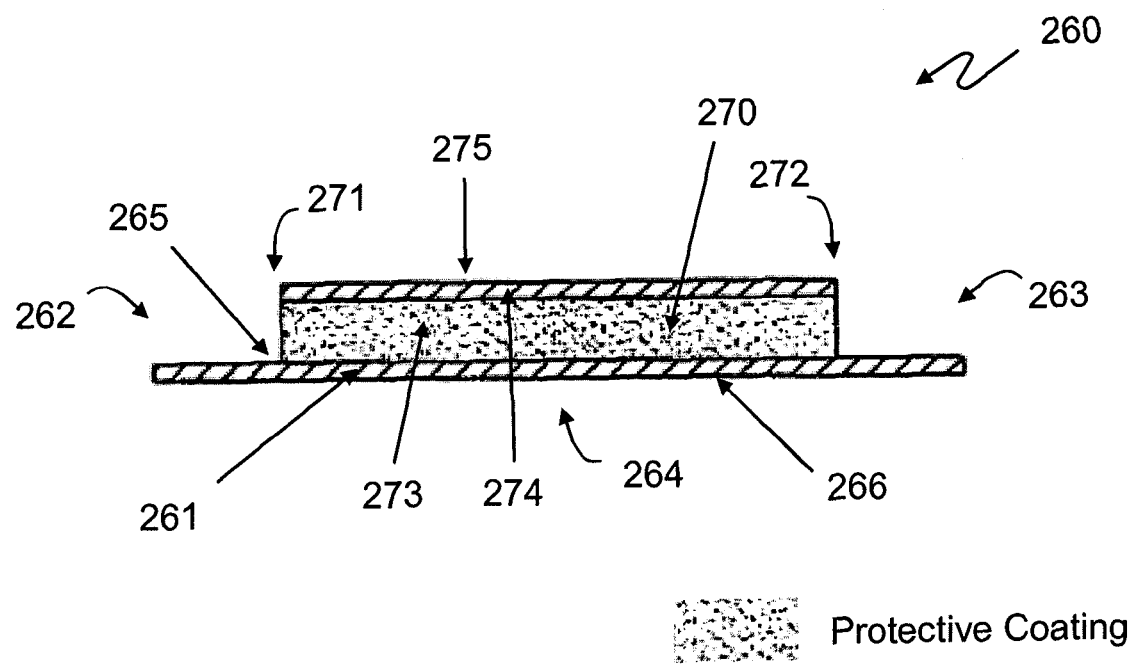
FIG. 56 is cut-away bottom view of a Doyle Shark Nasal Splint according to one aspect of the present invention.

The base 261 may be substantially flat and in the same plane, a depicted in FIGS. 44, 46, 47, and 53. Alternatively, a portion of the base 261 may be in a different plane. For example, FIGS. 49, 51, and 56 show a portion of the base 261 that is in a different plane; in FIGS. 49 and 51, this portion corresponds to the portion that resembles the shape of a shark's dorsal fin depicted in FIGS. 48 and 50.

The nasal splint 260 may also comprise a polymer coating on one or more or all of the surfaces of the nasal splint 260. Coating the nasal splint 260 in this manner serves to allow for ease of removal and to eliminate the possibility of bleeding. The coated splint does not adhere to any tissue, and prevents accumulation of adhesions, granulations, crusting, and mucus/blood. In addition, the coating will prevent adhesion to tissues which can cause bleeding upon removal, and prevent build-up of blood, or blood clots, to the device.

The nasal splint 260 may further comprise a tubular structure 270 on the first surface 265, as shown in FIGS. 43-47 and 52-55. The tubular structure 270 may extend between the first curved end 262 and the second curved end 263 of the base 261. The tubular structure 270 may comprise an open first end 271 and an open second end 272. The tubular structure may also comprise a lumen 273 extending between the first open end 271 and the second open end 272 such that the lumen 273 comprises an inner surface 274, and an outer surface 275.

Figure 45:
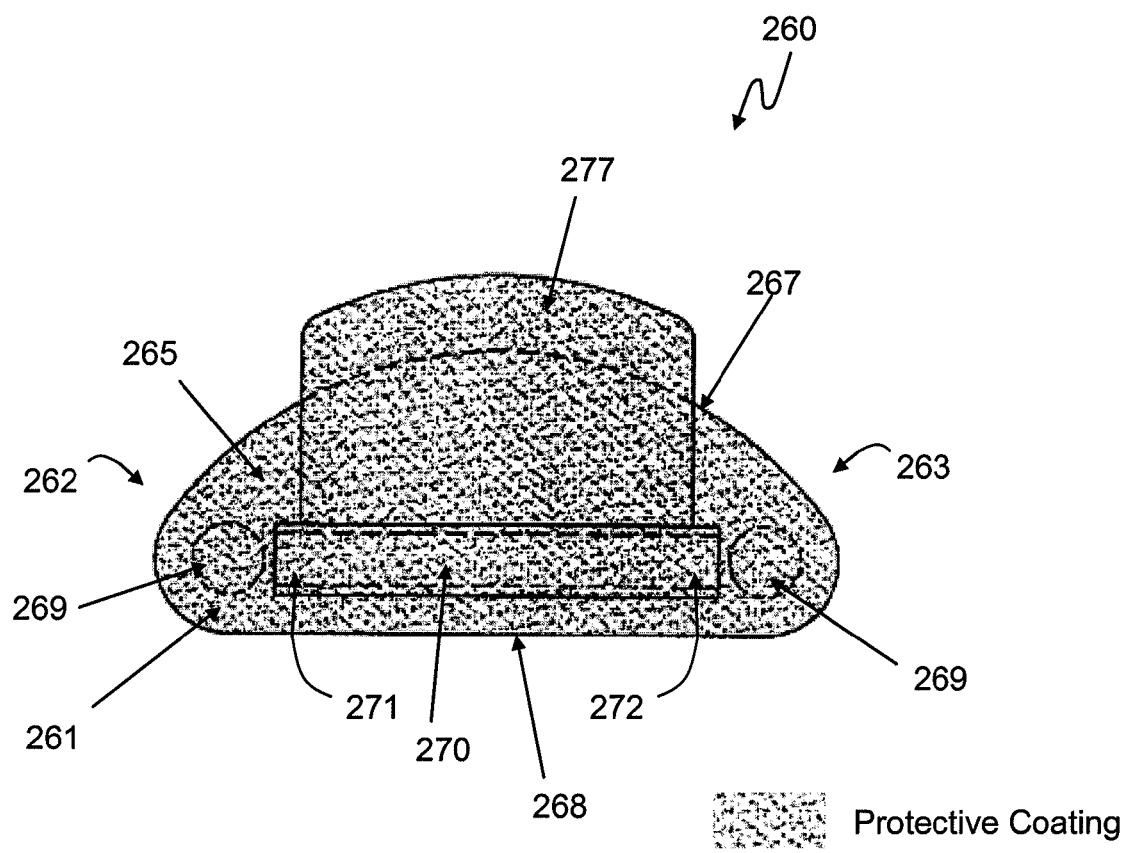
FIG. 45 is a side view of a nasal splint comprising a segment extending from the tubular structure of the splint according to one aspect of the present invention.

The tubular structure 270 may be of any length, but is limited by the distance between the first curved end 262 and second curved end 263 of the base 261. The tubular structure may also be located at any site between the first edge 267 and the second edge 268 of the base 261. For example, the tubular structure 270 may be adjacent to the first edge 267 as depicted in FIG. 43, or may be adjacent to the second edge 268, or anywhere between as depicted in FIGS. 45 and 54. The tubular structure 270 may be of a particular size such that it is simultaneously adjacent to both the first edge 267 and the second edge 268 of the base 261, as shown in FIG. 52.

Figure 44:
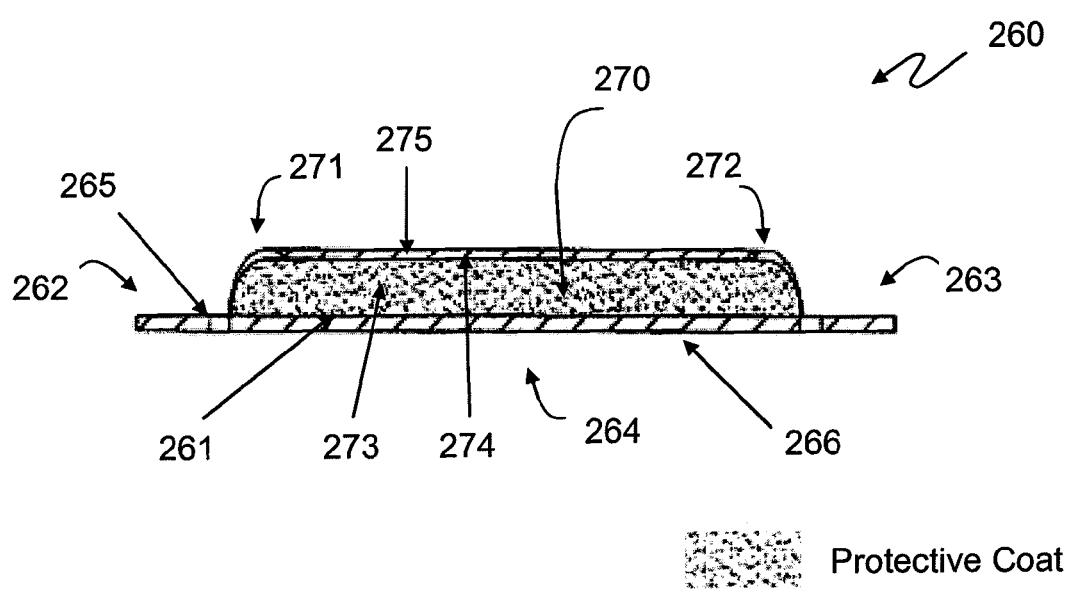
FIG. 44 is a cut-away bottom view of a nasal splint according to one aspect of the present invention.
Figure 52:
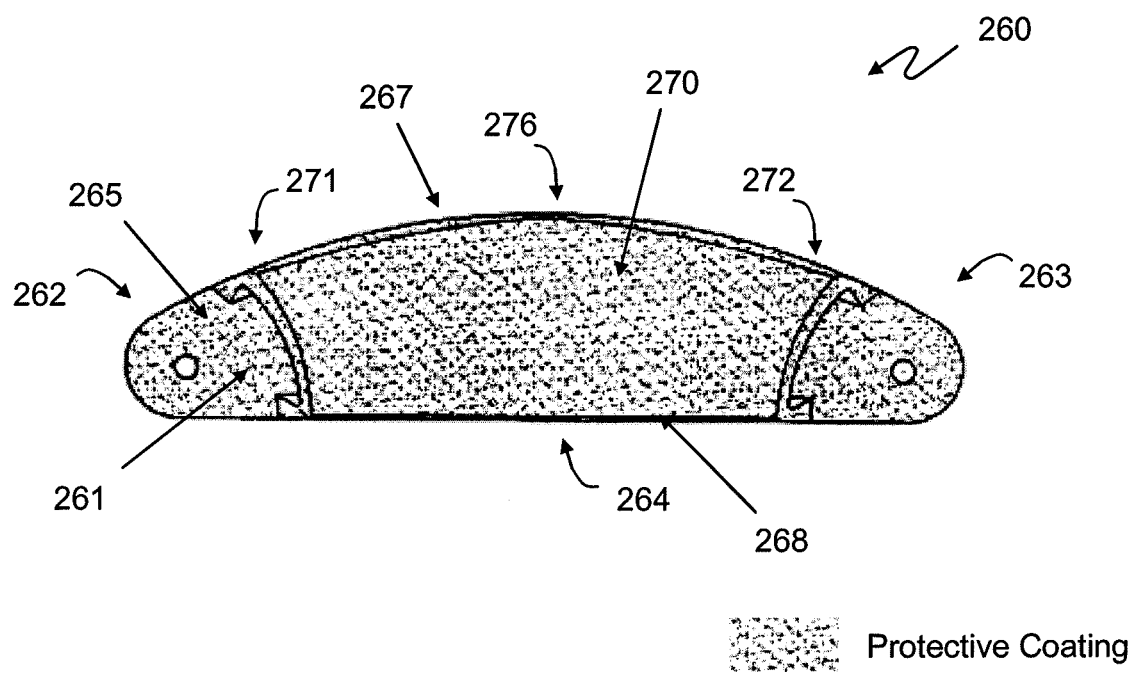
FIG. 52 is a side view of a Tellez Nasal Splint according to one aspect of the present invention.

The open first end 271 and the open second end 272 may be curved, for example, as shown in FIG. 43 or 52. The open first end 271 and the open second end 272 may also be angled, for instance, as shown in FIG. 44 or 53.

The tubular structure 270 between first open end 271 and the second open end 272 may comprise a curvature 276. The curvature 276 may be the same as the curvature of the first edge 267.

The tubular structure may additionally comprise a coating on one or more portions of the inner surface 274, the outer surface 275, or both the inner surface 274 and outer surface 275. Coating the tubular structure 270 in this manner serves to control mucus and granulation accumulation both internally and externally, as well as prevent adhesion to tissues which can cause bleeding upon removal, and prevent build-up of blood, or blood clots, to the stent. In certain embodiments, the entire inner surface 274 or outer surface 275, or both, may be coated.

The tubular structure may comprise a substantially flat segment 277 which extends from the tubular structure. The segment 277 may extend towards either the first edge 267 or the second edge 268 of the base 261. The segment 277 may be parallel with the base 261.

Yet another embodiment relates to the Tellez Nasal Splint or the Doyle Shark Nasal Splint comprising protective coating as described above (see FIGS. 52-55).

Thus, FIGS. 43-56 depict various embodiments of the nasal splints. For example, FIGS. 43 and 44 show a nasal splint 260 comprising a protective coating on its base surfaces 265 and 266, and a tubular structure 270 which comprises a protective coating on its outer surface 275 and inner surface 274. Also, the first open end 271 and the second open end 272 of the tubular structure 270 is curved, and the tubular structure comprises a curvature that is the same as the curvature of the first edge 267 of the splint.

Figure 47:
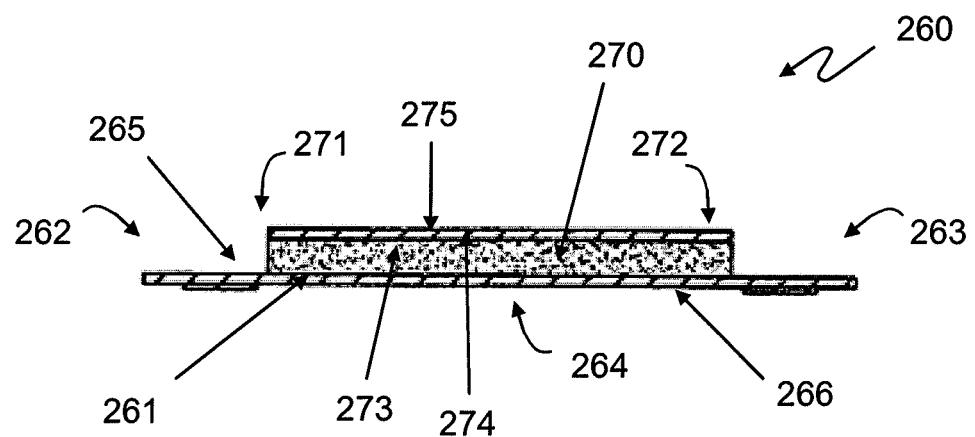
FIG. 47 is a cut-away bottom view of a nasal splint comprising a segment extending from the tubular structure of the splint according to one aspect of the present invention.

FIGS. 45-47 show a nasal splint 260 comprising a protective coating on its surfaces 265 and 266, and a tubular structure 270 which comprises a protective coating on its outer surface 275 and inner surface 274. Also, the first open end 271 and the second open end 272 of the tubular structure 270 is not curved, and the tubular structure between the first open end 271 and the second open end 272 is substantially straight. Further, the tubular structure 270 comprises a substantially flat segment 277 which extends from the tubular structure and is parallel to the 261 of the splint 260.

FIGS. 45-47 show a nasal splint 260 comprising a protective coating on its surfaces 265 and 266, and a tubular structure 270 which comprises a protective coating on its outer surface 275 and inner surface 274. Also, the first open end 271 and the second open end 272 of the tubular structure 270 is not curved, and the tubular structure between the first open end 271 and the second open end 272 is substantially straight. Further, the tubular structure 270 comprises a substantially flat segment 277 which extends from the tubular structure and is parallel to the 261 of the splint 260.

FIGS. 48-51 show a nasal splint 260 comprising a protective coating on its surfaces 265 and 266, and comprising a first edge 267 of the middle region 264 which comprises a portion that resembles the shape of a shark's dorsal fin. Further, the portion of the base 261 comprising a portion that resembles the shape of a shark's dorsal fin is not in the same plane as the rest of the base.

FIGS. 52 and 53 show the Tellez Nasal Splint comprising a protective coating on its surfaces 265 and 266.

Finally, FIGS. 54-56 show the Doyle Shark Nasal Splint comprising a protective coating on its surfaces 265 and 266.

While specific embodiments of the subject invention have been discussed, the above specification is illustrative and not restrictive. One skilled in the art will appreciate that numerous changes and modifications can be made to the invention, and that such changes and modifications can be made without departing from the spirit and scope of the invention. The full scope of the invention should be determined by reference to the claims, along with their full scope of equivalents, and the specification, along with such variations.

What is claimed is:

1. A nasal splint comprising an oblong-shaped base, the oblong base comprising
   a first curved end, a second curved end, and a middle region therebetween wherein middle region comprises a first edge and a second edge,
   a first surface, and a second surface,
   one or more holes through the first and second surfaces, and
   a protective coating that covers one or more portions of the first surface, second surface, or both the first and second surfaces, of the splint,
   wherein a thickness of the oblong base is greater proximate to the one or more holes than at other sites of the oblong base, and
   wherein edges of the one or more holes are level with the first and second surfaces.

2. The nasal splint of claim 1, wherein the protective coating is a polymeric coating.

3. The nasal splint of claim 2, wherein the polymer is parylene.

4. The nasal splint of claim 1, wherein the first edge of the middle region is curved or substantially straight.

5. The nasal splint of claim 1, wherein the first edge of the middle region further comprises a dorsal fin-shaped portion extending from the curvature of the first edge.

6. The nasal splint of claim 1, wherein the second edge of the middle region is curved or substantially straight.

7. The nasal splint of claim 1, further comprising a tubular structure on the first surface of the base, wherein the tubular structure extends between the first end of the base and the second end of the base, and wherein the tubular structure comprises: (i) a first open end; (ii) a second open end; (iii) a lumen extending therethrough having an inner surface an inner circumference; (iv) an outer surface; (v) an outer circumference; and (vi) a tubular wall between the inner surface and outer surface.

8. The nasal splint of claim 7, wherein the tubular structure is adjacent to the first edge of the middle region of the base, the second edge of the middle region of the base, or is in the center of the base.

9. The nasal splint of claim 7, wherein the first end of the tubular structure and the second end of the tubular structure are curved.

10. The nasal splint of claim 7, wherein the tubular structure between the first and the second end is curved.

11. The nasal splint of claim 7, further comprising a protective coating that covers one or more portions of the inner surface, outer surface, or both the inner surface and outer surface, of the splint.

12. The nasal splint of claim 11, wherein the protective coating is a polymeric coating.

13. The nasal splint of claim 12, wherein the polymer is parylene.

14. The nasal splint of claim 13, wherein the tubular structure further comprises a substantially flat segment that extends from the tube and is parallel to the base.

* * * * *